United States Patent [19]

Haas

[11] 4,167,870

[45] Sep. 18, 1979

[54] CHEMICAL TRACER METHOD OF AND STRUCTURE FOR DETERMINATION OF INSTANTANEOUS AND TOTAL MASS AND VOLUME FLUID FLOW

[76] Inventor: Rudy M. Haas, 8171 Forestlawn, Detroit, Mich. 48234

[21] Appl. No.: 843,792

[22] Filed: Oct. 20, 1977

Related U.S. Application Data

[60] Division of Ser. No. 395,135, Sep. 7, 1973, Pat. No. 4,055,083, and a continuation-in-part of Ser. No. 349,622, Apr. 9, 1973, Pat. No. 3,988,926, which is a continuation-in-part of Ser. No. 141,749, May 10, 1971, Pat. No. 3,727,048.

[51] Int. Cl.$^2$ .............................................. G01F 1/70
[52] U.S. Cl. ................................................. 73/194 M
[58] Field of Search ............ 73/19, 23, 194 E, 194 M; 23/232 R, 254 R, 232 E, 254 E; 422/78, 81

[56] References Cited

U.S. PATENT DOCUMENTS

| 3,435,659 | 4/1969 | Sternberg | 73/23.1 |
| 3,435,660 | 4/1969 | Sternberg | 73/23.1 |

*Primary Examiner*—Herbert Goldstein
*Attorney, Agent, or Firm*—Whittemore, Hulbert & Belknap

[57] ABSTRACT

Instantaneous mass flow rate of a component of interest in a flowing fluid is determined by structure for and method of introducing a tracer at a known mass flow rate into the flowing fluid, then analyzing for the concentration of the tracer and that of the component of interest in the mixed flowing fluid, and obtaining the product of the concentration of the component of interest, the reciprocal concentration of the tracer, and the mass flow rate of the tracer. To obtain the total mass flow of the component of interest, the instantaneous mass flow rate is time integrated over the desired period.

In addition to obtaining instantaneous and total mass flows of the component of interest, similar structures and methods are used for obtaining (1) volume flow, (2) mass flow of particulate matter, (3) linear velocity of the flowing fluid or the cross sectional area of the flowing fluid, (4) concentration values of the tracer and the component of interest in the presence of particulate matter by passing three signals through the flowing fluid, and (5) single average values for each concentration in a collected sample rather than obtaining continuous analysis data during flow time.

The case is considered where the introduced tracer undergoes a reaction when the reaction products are qualitatively and quantitatively analyzable.

7 Claims, 4 Drawing Figures

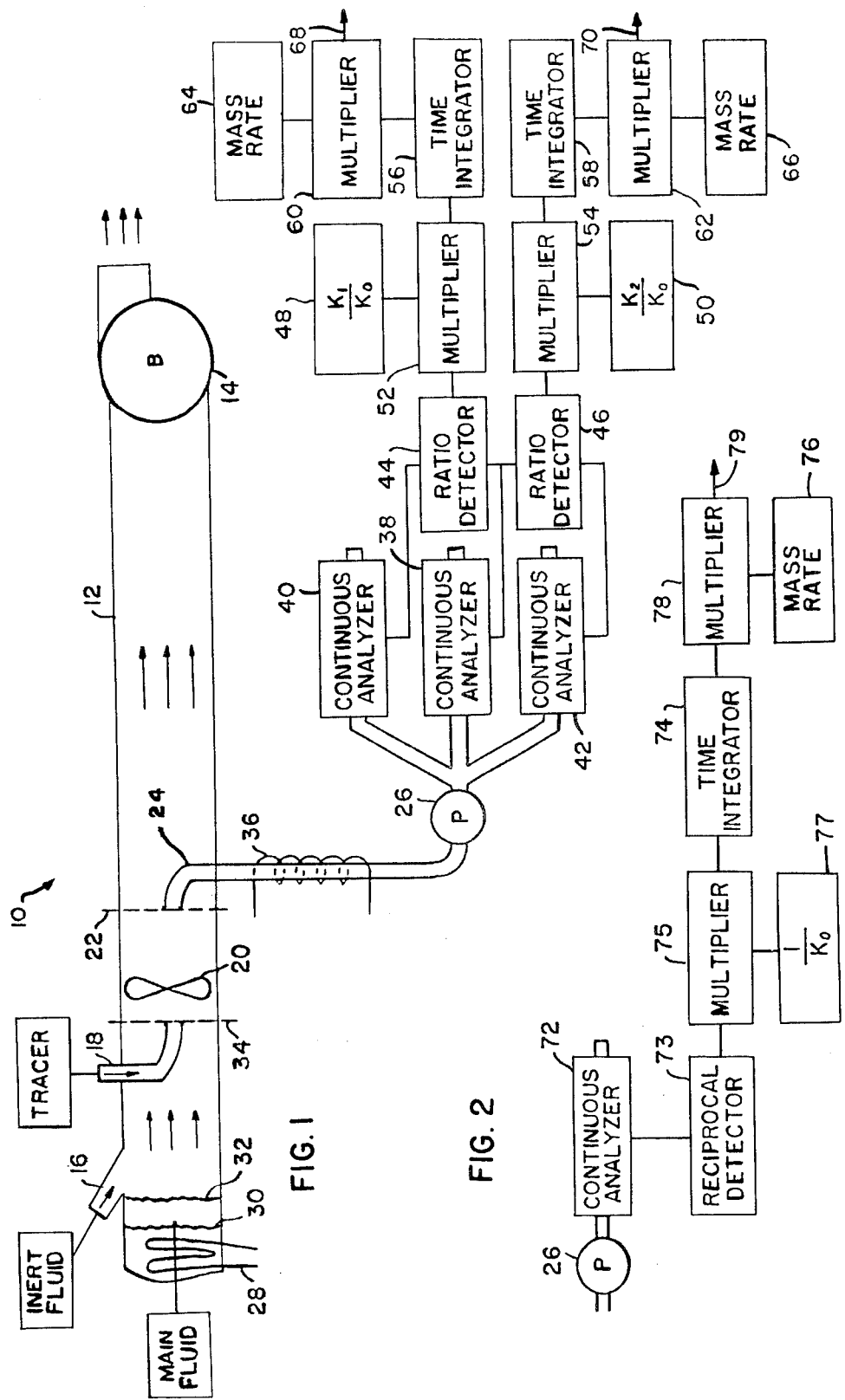

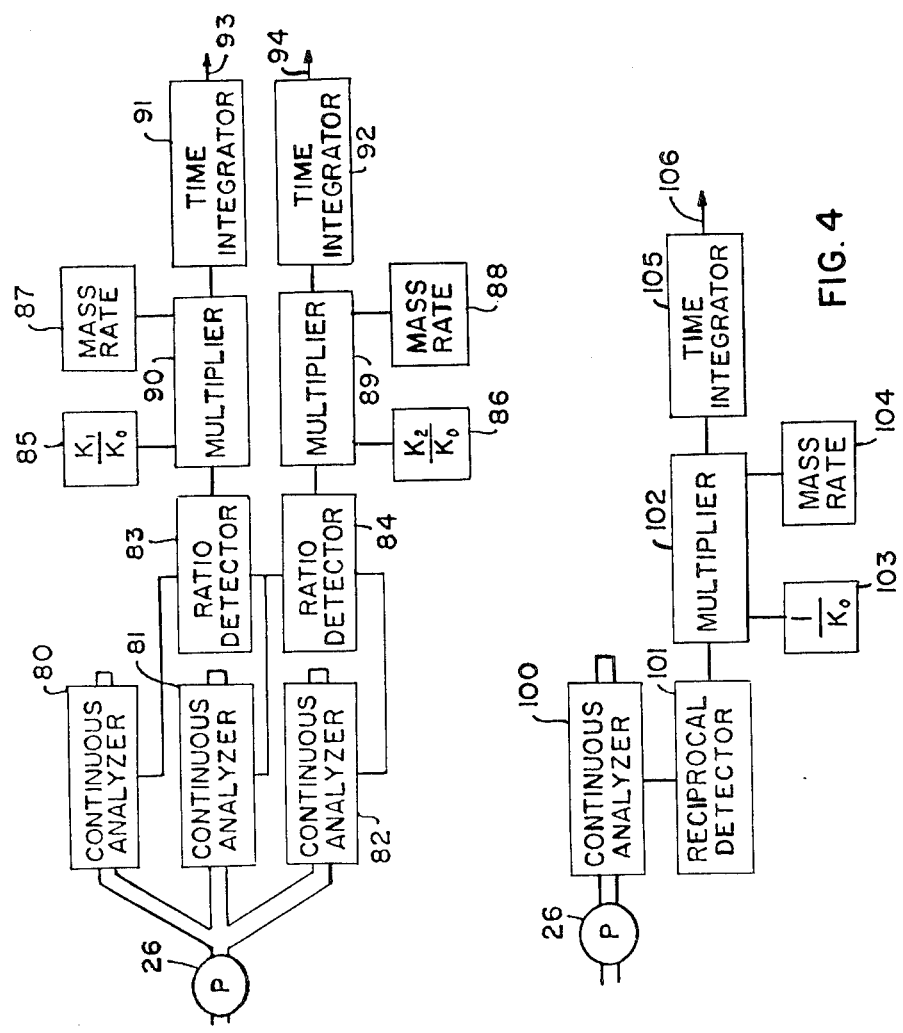

CHEMICAL TRACER METHOD OF AND STRUCTURE FOR DETERMINATION OF INSTANTANEOUS AND TOTAL MASS AND VOLUME FLUID FLOW

CROSS REFERENCE TO RELATED APPLICATIONS

This is a division, of application Ser. No. 395,135 filed Sept. 7, 1973 now U.S. Pat. No. 4,055,083.

This application is a Continuation-in-Part of my copending application Ser. No. 349,622, filed Apr. 9, 1973, now U.S. Pat. No. 3,988,926, entitled "Chemical Tracer Method and Structure for Determination of Instantaneous and Total Mass and Volume Fluid Flow," which application is a Continuation-in-Part of my application Ser. No. 141,749, filed May 10, 1971, entitled "Chemical Tracer Method of and Structure for Determination of Instantaneous and Total Fluid Flow", now U.S. Pat. No. 3,727,048, issued Apr. 10, 1973.

BACKGROUND OF THE INVENTION

1. Field of the Invention

The invention relates mainly to determination of mass and volume flow of selected components of a fluid and refers more specifically to a chemical tracer method of and structure for determination of total and instantaneous mass (or other mass dependent properties such as volume, energy, radioactivity, etc.) flow of selected fluid components in automobile exhaust pipes, smokestacks, pipe lines and the like. One of the advantages of the method and structure of the invention is that the volumetric flow rate, pressure and temperature of the fluid mixture does not have to be known in some cases during practice of the method with the structure disclosed.

2. Description of the Prior Art

In the past, most approaches to air pollution control through the measurement of total emission and regulation thereof by government agencies and the like have required a knowledge of both concentration and total volume of emission. It is preferable, however, to have knowledge of the total mass emission of each component of interest without the necessity of determining the total volume of emission. This is especially true in determining mass emission from industrial smokestacks, automobile tailpipes and industrial and community sanitary systems.

SUMMARY OF THE INVENTION

In accordance with the invention, instantaneous mass flow of selected components of interest in a flowing fluid mixture are determined by introducing a chemical tracer into the main fluid flow, mixing, then analyzing for the tracer concentration and the component of interest concentration, then multiplying the concentration of the component of interest by the reciprocal of the tracer concentration and the mass flow rate of the tracer introduced into the main fluid flow; for obtaining the total mass flow, this product is integrated with respect to time.

In determining total mass flow of one or more of the many components present, calculations and procedures become simpler if more of the following terms are held constant, i.e., pressure, temperature, and fluid flow rate of the mixture consisting of tracer and main fluid and the tracer mass flow rate therein. When the tracer introduction rate varies, difficulties are encountered which do not exist when the introduction rate is constant.

In addition to obtaining instantaneous and total mass flows of the component of interest, similar structures and methods are used for obtaining: (1) volume flow, (2) mass flow of particulate matter, and (3) linear velocity of the flowing fluid or the cross sectional area of the flowing fluid.

Collected samples in containers are also discussed, where only a single analysis of each component within the mixture needs to be made.

The use of a light beam having both a reference and at least one sample wavelength band where the reference wavelength band is not absorbed by a moving fluid but is absorbed by particles moving within the fluid, while the wavelength band of the sample or samples is absorbed by both the moving fluid and the particles within it is also disclosed. The advantage here is that the sample does not have to be preconditioned before analysis can be performed. Also, a method in which the introduced tracer undergoes a chemical reaction and the reaction products are analyzed both qualitatively and quantitatively to give data for calculating the mass flow rate of the component of interest is disclosed.

BRIEF DESCRIPTION OF THE DRAWINGS

FIG. 1 is a partially diagrammatic and partially block diagram of structure constructed in accordance with the invention particularly suited for determination of total mass flow and adaptable for determination of total volume flow and instantaneous values of either mass or volume in a flowing fluid by chemical tracer methods in accordance with the invention.

FIG. 2 illustrates a modification of the structure of FIG. 1 particularly suited to determining total and also adaptable for determining instantaneous volume flow by the method of the invention.

FIG. 3 illustrates a modification of the structure of FIG. 1 particularly suited to determining the total mass flow and also adaptable for determining total volume and instantaneous values of either mass or volume in a flowing fluid where the mass introduction rate of tracer can be variable in accordance with the invention.

FIG. 4 illustrates a modification of the structure of FIG. 2 particularly suited to determining total and also adaptable for determining instantaneous volume flow where the mass introduction rate of the tracer can be variable in accordance with the invention.

DESCRIPTION OF THE PREFERRED EMBODIMENTS

The structure 10 for determining the total mass flow, over a selected period of time, of a component of interest in a flowing fluid mixture is illustrated in FIG. 1. It includes a main fluid flow tube 12 through which the flowing fluid mixture to be analyzed is passed. The fluid to be analyzed may be drawn through the tube 12 by means of the blower 14 or similar apparatus to provide a uniform flow rate for the main fluid. Under some circumstances there may already be a pushing force present. If the flow in the main flow tube 12 is not sufficient to fill this tube, additional fluid, usually inert, may be introduced into the flowing fluid through the tube 16 connected to the tube 12 as shown. Thus, the fluid flow rate may more easily be maintained constant.

A tracer which disperses readily in the main fluid flow and is readily analyzable is introduced into the main fluid flow tube 12 through the tracer injection tube 18. The exact location of the tracer injection tube or tubes does not have to be as shown in FIG. 1 but it or they should be placed and operated in a manner to produce a uniform tracer concentration over the cross sectional area 22 in FIG. 1 or 3. The tracer can be introduced through tube 16, or it can be introduced prior to the site of the inert fluid inlet tube 16 but with the restriction that no fluid enters at the inert fluid inlet 18, or the tracer inlet 18.

The main fluid flow, inert fluid if any, and injected tracer are mixed by mixer 20. Theoretically the tracer is thus uniformly distributed over the cross section 22 of the main flow tube 12. A sample of the mixed tracer and main fluid and inert fluid if it was added is withdrawn from the main fluid flow tube 12 through the sample tube 24 and is passed to the pump 26. In place of removing a sample for analysis, an analyzing signal, e.g., electromagnetic radiation, can be transmitted from or into the main flow tube at the hypotheoretical cross sectional area 22 in order that no sample handling or conditioning becomes necessary.

Prior to the tube 16, a heat exchanger 28, a particle filter 30 and a condenser 32 can be provided to prevent volume changes, particle deposition, or condensation, respectively, before or in the analyzers. The flowing fluid mixture may be maintained at a constant temperature by the heater 28, and other heaters lining the main fluid flow tube. If needed, undesirable particles are filtered from the fluid and moisture is condensed from the fluid prior to introduction of the tracer thereinto at the cross section 34 of the tube 12. Since particles or condensation are only a disadvantage to the analyzer, their removal may be desired only on the portion of the sample undergoing analysis.

If the tracer is a fossil fuel which is also to be used for heat production as in a furnace (to be considered as a reactor for our purposes), it will be introduced into the reactor prior to the main fluid flow tube through which the reaction products pass.

If coal is the fuel, its mass introduction rate can be measured as it comes into the furnace, e.g., it can be brought to the furnace at a known mass rate, e.g., on a conveyor belt.

In addition, a heater 28, 36 or other may be provided anywhere in the apparatus 10 to maintain the temperature of the main fluid flow and/or sample substantially constant.

The sample of the tracer and main fluid is passed through the pump 26 to the continuous analyzers 38, 40 and 42. Analyzers 38, 40 and 42 for analyzing the concentration of tracer and the concentration of two components of interest in the main fluid flow respectively are well-known items of commerce and will not be considered in detail herein, except to say that the analyzers should be linear or should be linearized. The analyzers can be of a flow or non-flow rate dependent variety. Analyzers of the non-dispersive infrared or ultraviolet type are well suited to this type of analysis and may be purchased from The Beckman Instrument Company as Model 315, non-dispersive infrared analyzer. The continuous analyzers will provide an output signal which is proportional to and varies in accordance with the concentration of the tracer and components of interest in the main fluid flow tube 12 at cross section 22. If the output signal of the analyzer used is not linear with respect to the concentration, a linearizing electronic circuit, a calibration curve equation along with a computer, or in the case of a photometric analyzer, a signal proportional to a log of the reciprocal transmission may be used.

The signals from the analyzers 38 and 40 and from the analyzers 38 and 42 are passed to ratio determining circuits 44 and 46 from which signals proportional to and varying in accordance with the ratio of the concentration of the separate components of interest to the concentration of the tracer of the flowing fluid mixture at the cross section 22 are provided. The ratio signals are then multiplied by desired proportionality factors between circuit parameter values, $K_0$, $K_1$ and $K_2$ which are constants if the analyzer output signal is linear or become constants when the analyzer signal is linearized from circuits 48 and 50 in multipliers 52 and 54. The signals from the multipliers 52 and 54 are then integrated over the time the total masses of the components of interest are desired in the integrators 56 and 58. The integrated signals are subsequently multiplied in multipliers 60 and 62 by signals proportional to the constant mass rate of injection of tracer into the main fluid from circuits 64 and 66 to provide output signals on conductors 68 and 70 representative of the total mass of the components of interest during the time of integration. If necessary, the output signals are multiplied by proportionality factors to standardize the circuits due to the units of measurement being used.

In the apparatus of FIG. 1, the tracer is introduced at a known constant mass rate in order to measure the total mass flow of the component of interest over the time period of interest. If the volumetric fluid flow rate of the mixture is constant, the concentration of the tracer can be brought outside the integral sign where the ratio of the mass introduction rate of the tracer to its resulting concentration is a constant. This apparatus can also be used to obtain the total volume flow of a fluid by setting the concentration of the component of interest, $C_1$, equal to 1. In addition, the apparatus can also be used to obtain instantaneous mass and volume flow rates by not integrating over a period of time. If the mass introduction rate is constant for the tracer, the flow rate of the fluid in the main flow tube does not have to be constant, but it is preferred that it be constant. If the introduction rate of the tracer varies with time, the fluid flow rate should be as constant as possible for greatest accuracy, using the prescribed mathematical equation for the calculation. A time delay device or its equivalence must be present in order to relate, for the purpose of calculating the concentrations of both the tracer and the components of interest to the known mass introduction rate of the tracer responsible for its concentration at the designated cross sectional area. In other words, for greatest accuracy, the tracer mass introduction rate must equal the mass flow rate of the tracer passing the cross sectional area most of the time, not necessarily at the same instant of time, but this difference in time must be determinable if it is significant in the calculations. The tracer introduction rate may be based on the required concentration needed to give satisfactory analytical results for the analyzer to be used. In the apparatus of FIG. 3, the tracer may be introduced at a known variable mass rate.

With a variable mass flow rate resulting from a variable mass introduction rate of tracer, a sample of the tracer, main fluid, and inert fluid if needed, is passed through the pump 26 to the continuous analyzers 80, 81 and 82. Analyzers 80, 81 and 82 are equivalent to the analyzers 40, 38 and 42 in FIG. 1.

The signals from the analyzers 80 and 81 and from the analyzers 81 and 82 are passed to ratio determining circuits 83 and 84, which are equivalent to the ratio determining circuits 44 and 46 in FIG. 1, from which signals proportional to and varying in accordance with the ratio of the concentration of the separate components of interest of the concentration of the tracer of the flowing fluid mixture at the cross section 22 are provided. Each of the output signals from ratio detectors 83 and 84 are then multiplied in multipliers 89 and 90 by the desired proportionality factors between circuit parameter constants, $K_0$, $K_1$ and $K_2$ from circuits 85 and 86, and by signals proportional to the mass rate of introduction of tracer into the main fluid from circuits 87 and 88. The signals from the multipliers 89 and 90 are then integrated in the integrators 91 and 92 to provide output signals on conductors 93 and 94 representative of the total mass flow of the components of interest during the time of integration.

When, throughout the specification, any mention is made in reference to a constant mass introduction rate, constant volumetric flow rate, constant temperature and pressure, and the like, it is to be understood that any slight variation from a constant value will not result in the method of procedure being inoperative or useless but will usually result in an error in the obtainable results, the magnitude of the error will depend on the extent of the deviation from a true constant value. Furthermore, unless otherwise specified, all operations are considered, at least as far as it was mentioned, to be carried out at the same cross sectional area and at the same instant of time in regard to supplying data to the equations being used. It is realized at this time that there are other more appropriate locations and times where data can be collected easier.

It is also possible, rather than using a ratio detector, as shown in FIGS. 1 and 3 of the drawings, to use in place thereof an inverter to obtain a signal representative of the reciprocal of the concentration, which concentration is obtained from the continuous tracer analyzer, which signal can then be split among a number of multipliers, one multiplier for each component of interest. The resulting output signal from the multipliers is representative of a ratio of the concentration of the component of interest and the concentration of the tracer. By setting the concentration signal of the component of interest equal to 1, when using an inverter or ratio detector the same electronic circuitry can be used for the total volume flow determination as was used for the total mass flow determination.

The tracer, which may be continuously analyzed as carbon dioxide and injected at a known mass rate of a fossil fuel, equivalent to a known mass rate of carbon dioxide, when the main fluid is air and the tracer oxidation products are combustion gases, should pass the cross sectional area 22 at the same rate as the tracer is introduced into the main fluid flow tube 12 at the cross section 34, but if the time difference between tracer introduction and removal (or direct in tube analysis) is significant, this time must be considered in relating the tracer mass introduction rate to the concentration it produces for its equations where it is used.

The fluid flow to the continuous analyzers 38, 40 and 52 must originate from the same volume in the main fluid flow tube 12, and should arrive at each analyzer for analysis at the same time. As before, the flow time for the sample to pass from the main flow tube to the point of analysis in the analyzer must also be considered when substituting data in the proper equations; otherwise, part or all of the data at the analyzers must be stored and subsequent calculations must be conducted with the stored data sometime in the future.

The introduced tracer may be a pure component or a mixture having a pure tracer component plus an inert ingredient. The "pure" tracer component itself can be a mixture having a known composition, with or without inert ingredients, e.g., a fossil fuel. In addition, the tracer must be accurately qualitatively and quantatively analyzable on a continuous basis and should not undergo a chemical change unless the extent of the chemical reaction is known and its products are easily analyzable. An example of this latter would be the use of a fossil fuel which undergoes a combustion reaction and the products such as carbon dioxide, are analyzed.

A tracer such as helium or one of the inert gases is useful where the tracer must be stable at a high temperature such as occurs in the burning of fossil fuels in air, since it is not present in the air originally. Freons, added after combustion, are useful in analyzing combustion gases. Carbon tetrafluoride is especially useful because of its inertness and its sharp infrared spectra peaks located away from most of the other wavelengths of the other products of combustion.

When a constant introduction rate is referred to for the tracer, an effectively constant mass injection is to be thought of, i.e., periodic injection with mixing to give what is equivalent to an actual constant mass injection, be considered the same for our purposes. The tracer component which is to be used, will of course depend on the overall system in which it is to be introduced, e.g., it can be (1) a stable or unstable element, or compound, (2) one that fluoresces, phosphoresces, or emits radiation or particles, or (3) one that absorbs mass or electromagnetic radiation or the like, or particles such as neutrons, protons, positrons, or the like. The physical state of matter of the tracer would not have to be the same as that already present in the main fluid flow tube, e.g., a liquid, soluble gas or solid can be injected into a liquid.

The linear flow velocity in the sampling line 24 does not have to be equal to that of the linear flow velocity in the main fluid flow tube 12, but it should be constant and preferably greater than that in the main fluid flow tube rather than slower, but not excessively greater, otherwise fluid far removed of what is at the cross sectional area 22 will be removed.

If the flow is much slower than that in the main flow tube, large, sudden concentration changes may not register accurately enough, thereby giving results very different than what is actually in the main flow tube. Isokinetic sampling usually would be preferred.

The sample analysis can be done directly on the main flowing fluid, e.g., by passing a beam of electromagnetic radiation through it where both the tracer and component of interest are absorbed at certain wavelengths. In addition, conditions which are established in the standardization of the analyzers 38, 40 and 42 such as temperature and pressure must not vary before the unknown mixtures have been analyzed.

The pump 26 for the continuous analyzers should be of a non-contaminating and non-corrosive material. A diaphragm-type pump is generally satisfactory. Other types of pumps may be required to maintain consistency in flow in both the main fluid flow tube 12 and in the sample flow tube.

In addition to analyzers of the spectrophotometric type, etc., those of an electrode type such as a calcium or water hardness specific ion electrode mainly for liquids are also being considered. In addition, electrodes for gas monitoring are also suitable, if available, since they can also be used to determine concentration (i.e., activity) directly when in conjunction with an E.M.F. measuring circuit.

Where it is stated that a tracer is introduced at a known mass rate, in addition to what is usually meant, it is also understood to mean that the tracer can enter the flowing fluid stream: (1) due to formation of a substance as a result of a physical or chemical reaction, resulting from the introduction of energy, such as electricity, heat, radiation, etc., into the flowing main fluid or (2) by decomposing a substance not part of the flowing fluid but in contact with it, such as dissolution of an electrode with electrical energy, always at a known rate.

The introduced tracer can also be a mixture of two or more tracers, where each of the tracers is used for determining the mass of one or more components of interest. One of the advantages would be where two or more multicomponent analyzers, e.g., mass spectrometer and chromatographs are used where each can analyze the tracer and one component of interest with ease while the other component may be difficult to analyze with the same analyzer.

Thus, in operation of the apparatus 10, a fluid such as automobile engine exhaust gas is passed into the main fluid flow tube 12 past the temperature control structure 28 where the temperature is made constant. Particles can be filtered from the exhaust and any moisture therein is condensed by the filter 30 and condensation structure 32, or it may be made constant by adding a stream of water vapor and the like.

If the quantity of exhaust gas is not sufficient to provide a constant or almost constant flow rate in the main fluid flow tube 12, an additional inert gas can be injected into the fluid flow tube 12 through the tube 16 sufficient to provide a constant total fluid flow through the main fluid flow tube 12, if this is needed or preferred.

On passing the cross section 34 in the main fluid flow tube 12, a tracer chemical such as carbon dioxide is injected into the main fluid flow at a known mass rate. A known mass rate may be maintained by the use of known flow rate devices such as a critical orifice, a constant diffusion permeation tube, a mechanical metering device, or a constant energy addition producing a constant mass rate of another substance, e.g., an electrochemical decomposition, etc., which will not be considered in detail herein.

The main fluid flow and tracer are mixed by mixer 20 to provide a uniform mixture at the cross section 22 of the main fluid flow tube 12. After passing the sample tube 24 at the cross section 22, the fluid mixture is usually passed through the blower or pump 14 and is exhausted from the main fluid flow tube 12. A blower is usually satisfactory for gases and a transfer pump for liquids. In some cases, no pumping system 14 is necessary because of some other driving force.

The sample of the mixed main fluid flow and tracer is passed through pump 26 to the continuous analyzers 38, 40 and 42 which are used to analyze the concentration of the tracer and the components of interest in the flowing fluid mixture. The electrical signals from the analyzers are passed to the ratio determining circuits 44 and 46, so that out of the ratio determining circuits 44 and 46 a signal equal to a ratio of the concentration of the components of interest to the tracer concentration in the flowing fluid mixture is provided.

These ratio signals are then multiplied by signals from the circuits 48 and 50 to compensate for the electrical differences in the analyzer circuits and are subsequently integrated by integrators 56 and 58 over the time that the total mass flow of the components of interest of the flowing fluid mixture is desired. The integrated signals from the integrators 56 and 58 are subsequently multiplied in the multipliers 60 and 62 by a signal representing the mass flow rate of the tracers 68 and 66 to provide the conductors 68 and 70 with a signal representing the total mass of the components of interest flowing in the flowing fluid mixture over the time of integration. This electronic signal can be fed to a digital readout, a paper printer, a computer, etc., or can be used to actuate an electronic switch.

Under the circumstance where the mass introduction rate of the tracer is not constant over the time period of integration, the tracer introduction rate must be multiplied by the ratio of the analyzer signals before integration, or both the tracer concentration and tracer introduction rate can be outside the integral sign for a constant fluid flow rate of the flowing fluid mixture.

The operation of the apparatus 10 can be mathematically shown to be theoretically correct. Thus, the relationship of mass ($m_1$), volume ($V_1$), and concentration ($C_1$), of a component of interest, with concentration expressed as mass per unit volume, is given below:

$$m_1 = C_1 V_1$$

The same relationship holds for the tracer component and is shown by the equation:

$$m_0 = C_0 V_0$$

Since the volume of tracer component and the component of interest in the sample are the same, V is the same as indicated by the equation:

$$V_1 = V_0 = V$$

Therefore, $$m_1 = \frac{C_1}{C_0} m_0$$

wherein $C_1$ and $C_0$ are both considered to be at the same temperature and pressure since both are referred to the same uniform composition which therefore is considered to be the same chemically and physically throughout. The units for the concentration terms are mass per unit volume, if other than these units are used proportionality factors would be needed.

The instantaneous mass flow rate of the component of interest, that is, $$\left(\frac{dm_1}{dt}\right)$$

passing through the cross sectional area 22 can be expressed as a function of $C_1$, $C_0$ and $$\left(\frac{dm_0}{dt}\right)$$

where $$\left(\frac{dm_o}{dt}\right)$$

is the instantaneous mass flow rate of the tracer, in units of mass per unit time, according to the equation:

$$\left(\frac{dm_1}{dt}\right) = \frac{C_1}{C_o}\left(\frac{dm_o}{dt}\right)$$

In this equation, $$\frac{C_1}{C_o}$$

is the proportionality factor relating mass of the tracer component transferred across the cross sectional area 22 to the mass of the component of interest also transferred across the same area where some, all, or none of the above four values may be time dependent.

The total mass flow of component one, that is, $m_1$ from $t_1$ to $t_2$, is obtained by the integration of the above equation to give:

$$\int_{(m_1)_{t_1}}^{(m_1)_{t_2}} dm_1 = \int_{t_1}^{t_2} \left(\frac{dm_o}{dt}\right)\frac{C_1}{C_o} dt$$

If the mass introduction rate of the tracer is not constant, then the total fluid flow rate should be constant, nearly constant, or changing slowly. It is then possible to relate the mass introduction rate of the tracer in the above equation to the concentration of the tracer it produces. If there is a large change in the flow rate of the fluid in a short period of time, collection and use of data with a high degree of accuracy becomes difficult. This is the case with both a constant and a variable mass introduction rate of tracer.

From this equation it is evident that in a system with a constant volumetric flow rate of the mixture, the ratio of $$\left(\frac{dm_o}{dt}\right)C_o$$

is a constant in both cases, by definition, i.e., $$\left(\frac{dV}{dt}\right) = 0,$$

(1) where the mass introduction rate of the tracer is constant, and (2) where the introduction rate is not constant but where the analyzed concentration is related back to what the mass introduction rate, $$\left(\frac{dm_o}{dt}\right)_o,$$

was that produced it.

Since the mass flow rate of the tracer through the cross sectional area 22, $$\left(\frac{dm_o}{dt}\right),$$

can be adjusted to be and remains the same as the mass introduction rate of the tracer $$\left(\frac{dm_o}{dt}\right)_o$$

if the mass introduction rate of the tracer is constant, that is to say, $$\left(\frac{dm_o}{dt}\right)_o = \text{a constant.}$$

Therefore, $$(m_1)_{t_2} - (m_1)_{t_1} = \left(\frac{dm_o}{dt}\right)_o \int_{t_1}^{t_2} \frac{C_1}{C_o} dt$$

where $(m_1)_{t_1} - (m_1)_{t_2}$ represents a difference in mass of the component of interest passing through the cross sectional area 22 from time $t_1$ to $t_2$.

Under the actual flow conditions wherein variations of flow in the main fluid flow tube occur, it is difficult to maintain the tracer mass introduction rate $$\left(\frac{dm_o}{dt}\right)_o$$

equal to the mass flow rate of the tracer through the cross sectional area 22.

When restrictions are placed on the flow system such as a constant temperature and pressure or a constant volumetric flow rate, the volume being considered is that volume between the tracer introduction site and the cross sectional area where analysis occurs either directly in the main flow stream, or at an analyzer or a collecting container at the end of a sampling line attached to the main flow tube.

If the distance between the point of introduction of the tracer and the point at which the sample is removed is small in the presence of good mixing, or there is no extended period of flow stoppage or fast variations in flow rate, especially if they occur frequently, the difference between $$\left(\frac{dm_o}{dt}\right)_o \text{ and } \left(\frac{dm_o}{dt}\right)$$

usually will not be great. In this regard, it is desired to keep $$\left(\frac{dm_o}{dt}\right)$$

constant at some one known value.

Since the ratio $$\frac{C_1}{C_o}$$

varies with time, it is necessary to take the ratio of the analyzer output signal, usually voltage, of two analyzers, which must be of the continuous type for concentrations that vary, one for the tracer and one for each of the components of interest whose total mass flow in the time interval $t_1$ to $t_2$ is to be determined. The output of each analyzer is then multiplied by a proportionality factor, K, such that if voltages $v_1$ and $v_2$ are the voltages from the analyzers, the following equation is true:

$$\frac{C_1}{C_o} = \frac{k_1}{k_o}\frac{v_1}{v_o}$$

For the sake of simplicity, the proportionality factors should be made equal so they cancel out.

Since the element of volume for both the tracer and the component of interest is the same, the rates of concentrations can be written as the ratio of their masses present in the same unit of volume, i.e.:

$$\frac{C_1}{C_o} = \frac{\frac{m_1}{V}}{\frac{m_o}{V}} = \frac{m_1}{m_o}$$

but since this is a disadvantage because concentrations are easier to obtain than mass, masses are not used, especially on a continuous basis. In the above equation, V is the total volume.

In addition to stating these concentration ratios as voltage or current ratios (assuming the proportionality factors $k_1$ and $k_0$ are equal), they can be written as any ratios which are proportional to the concentration or mass ratios, e.g., in the case of absorption of electromagnetic radiation, nuclear radiation, etc., where $$\frac{I_1}{I_o},$$

absorption per unit time intensity ratio, is to be used:

$$\frac{C_1}{C_o} = \frac{k_1 I_1}{k_o I_o}$$

In addition to expressing the concentration in units of mass per unit volume, they can also be expressed as a volume fraction, percent volume, parts per million by volume, etc., all multiplied by the density of the component of interest and usually a proportionality factor, e.g.:

$$\frac{mass_1}{volume_T} = \frac{density_1 \; volume_1}{volume_T} = \frac{D_1 V_1 10^6}{10^6 V_T} = \frac{D_1}{10^6} ppm_1$$

where $ppm_1$ refers to parts per million of component 1 expressed in units of volume, with T representing total.

The resulting proportionality signal, equal to the ratio of the above concentrations, is first multiplied by the mass injection rate of the tracer and then integrated over the time interval $t_1$ to $t_2$. If the mass injection rate of the tracer is constant, proportionality signal can first be integrated and then multiplied by the constant mass flow rate of the tracer $$\left(\frac{dm_o}{dt}\right)$$

which is equal to $$\left(\frac{dm_o}{dt}\right)_o$$

i.e., the tracer mass introduction rate, which is known. The result of this final multiplication is the total mass flow value of the component of interest which has passed through the cross sectional area 22 between the time $t_1$ and $t_2$. A constant flow is considered to mean not changing. The flow can be different in linear velocity along the path of travel thereof since if the cross sectional area is reduced, the linear fluid velocity is increased through this area. By knowing the volumetric flow rate, either the linear velocity or cross sectional area can be determined as long as the other is known.

In the case where the mass flow rate of the tracer, the total pressure and temperature are all held constant, the volumetric flow rate is also constant, assuming ideal fluid behavior, which assumption is usually valid for most fluids wherein only a slight molecular interaction is present. As a result of this constancy in the physical conditions of the tracer concentration, $C_0$, this term can be brought out in front of the integral sign, so that the above final equation for determination of total mass flow becomes the equation indicated below:

$$(m_1)_{t2} - (m_1)_{t1} = \left(\frac{dm_o}{dt}\right)_o \frac{1}{C_o} \int_{t_1}^{t_2} C_1 \, dt$$

This equation is true also if the mass introduction rate of the tracer were not constant since $$\left(\frac{dV}{dt}\right) = \left(\frac{dm_o}{dt}\right)_o \frac{1}{C_o}$$

equals a constant independent of the tracer mass flow rate or its concentration, i.e., the volumetric flow rate in the main fluid flow tube 12 is contant:

$$(m_1)_{t2} - (m_1)_{t1} = \left(\frac{dV}{dt}\right) \int_{t_1}^{t_2} C_1 \, dt$$

If $C_1$ is also constant under the same conditions of a constant volumetric flow rate of the flowing fluid mixture; that is, if the mass emission rate of component 1, i.e., $$\left(\frac{dm_1}{dt}\right)$$

from a source is constant, $C_1$ can also be brought in front of the integral sign and only an integration of the time differential is necessary, so that the final total mass flow equation becomes:

$$(m_1)_{t_2} - (m_1)_{t_1} = \left(\frac{dm_o}{dt}\right)_o \frac{C_1}{C_o} (t_2 - t_1)$$

If the mass emission rate of the component of interest is constant at the source of the smokestack, etc., its concentration can still vary, since the volumetric flow rate of the fluid mixture at the source can continuously undergo change. If sufficient inert fluid is added to the main flow tube to produce a constant volumetric flow rate of the fluid mixture, the concentration of component 1 becomes constant for the specified condition.

In the case where the volumetric flow rate of the fluid flow mixture at a constant temperature and pressure is constant.

$$\left(\frac{dm_o}{dt}\right) C_o$$

is also constant. In such cases, the main volumetric flow can be calibrated first for total volume flow with the equation $$\left(\frac{dm_o}{dt}\right) \frac{1}{C} (t_2 - t_1).$$

The concentration of the component of interest can then be obtained and integrated over the time of $t_1$ to $t_2$. The product of this total volume and the average concentration of $C_1$ will then give the total mass of component 1. In combustion processes, the fuel mass or a constant fraction thereof could be used as the source of the mass of the injected tracer and the above volume or mass determination can be made. With such volume or mass determinations, only approximate values can be obtained if carbon particles are produced at a sufficient rate and not entered into the appropriate mathematical equation.

Instantaneous mass or volume flow rates can be determined by the tracer introduction method with knowledge of the mass introduction rate of the tracer component or its equivalent, its concentration (in units equivalent to mass per unit volume), and where in the flowing fluid the introduction occurred in order that its concentration can be determined in that unit of volume.

For instantaneous mass flow determinations, the following equation is used along with the aforementioned requirements:

$$\left(\frac{dm_1}{dt}\right) = \left(\frac{dm_o}{dt}\right) \frac{C_1}{C_o}$$

The instantaneous mass flow rate of at least one component of interest in a flowing fluid mixture can be determined by the injection of an analyzable tracer component at a known mass rate into the flowing main fluid, mixing the tracer with the main fluid flow, passing the mixture of the tracer and the main fluid through a cross sectional area, analyzing the mixture at said cross sectional area to determine the concentration of the tracer and at least one component of interest in the mixture, obtaining the instantaneous mass flow rate of the tracer across the cross sectional area, obtaining the ratio between the component of interest concentration and the tracer concentration, and obtaining the product of said ratio and said mass flow rate of the tracer through the cross sectional area in accordance with the formula:

$$\left(\frac{dm_1}{dt}\right) = \frac{C_1}{C_o} \left(\frac{dm_o}{dt}\right)$$

where $$\left(\frac{dm_1}{dt}\right)$$

is the instantaneous mass flow rate of the component of interest, $$\frac{C_1}{C_o}$$

is the ratio of the concentration of the component of interest to the concentration of the tracer at said tracer mass flow rate and $$\left(\frac{dm_o}{dt}\right)$$

is the mass flow rate of the tracer through the cross sectional area. Both concentrations are to be used in units of mass per unit volume.

For instantaneous volume flow determination, in addition to the above, the temperature and pressure at the time when the concentration is determined and at the time the instantaneous volume flow is desired, are also needed if they undergo a change, along with the basic equation:

$$\left(\frac{dV}{dt}\right) = \left(\frac{dm_o}{dt}\right) \frac{1}{C_o}.$$

The instantaneous volume flow rate of a flowing main fluid mixture can be determined by the injection of an analyzable tracer component at a known mass rate into the flowing main fluid, mixing the tracer with the main fluid, passing the mixture of the tracer and the main fluid through a cross sectional area, analyzing the mixture from the cross sectional area to determine the concentration of the tracer, obtaining the concentration of the tracer, obtaining the product of the reciprocal of the tracer and the concentration mass flow rate of the tracer through the cross sectional area in accordance with the formula $$\left(\frac{dV}{dt}\right) = \left(\frac{dm_o}{dt}\right) \frac{1}{C_o}$$

wherein $$\left(\frac{dV}{dt}\right)$$

is the instantaneous volume flow rate of the flowing main fluid, $$\left(\frac{dm_o}{dt}\right)$$

is the mass flow rate of the tracer through the cross sectional area, and $C_0$ is the concentration of the tracer in units of mass per unit volume, each of the units of mass, volume and time should be the same throughout the equation.

When the tracer component used for introduction undergoes a chemical or nuclear reaction it becomes necessary to determine if the extent of the reaction is significant at the time of analysis for obtaining the desired accuracy. If the extent of the chemical reaction is sufficient so it cannot be ignored for the accuracy desired, calculations are directed either to (1) express the concentration of both the unreacted original tracer material and one or more of its decomposition products, all in terms of the originally introduced tracer material, or (2) express both the concentration of the unreacted introduced material and under some conditions that of one or more decomposition products, all in terms of the concentration of one of the designated atom-containing decomposition products. The first approach would be to determine the concentration of all components present at a significant concentration which contain the same atom as the designated atom in the injected tracer.

In some cases the tracer is already part of the original system, for example, in a combustion process where the fossil fuel or its decomposition products act as the introduced tracer in addition to its use as a heat (including pressure at times) producing substance. Here the introduction is into a reactor which may be a furnace, an engine, etc. Consideration of the fuel or its decomposition products as the tracer, is all a matter of choice. In this case, the reactants would be mainly hydrogen-carbon compounds and oxygen with only carbon dioxide and water being formed (assuming complete combustion and only matter containing hydrogen, carbon and oxygen as the reacting starting materials).

Commercial fossil fuels may contain small amounts of other products besides carbon and hydrogen, e.g., sulfur, phosphorus, etc. as a result, other products containing these can be formed as part of the decomposition products. Since complete combustion usually does not occur for fossil fuel, other carbon containing compounds in addition to carbon dioxide exist at a significant concentration as a result of a combustion reaction. They must also be analyzed and considered in the appropriate calculations if a significant error would result in its absence. These products would most likely be carbon monoxide, elemental carbon, newly formed hydrocarbons, oxygenated hydrocarbons, etc., and products containing various amounts of other atoms in addition to those of carbon, hydrogen and oxygen (e.g., $NH_3$, $H_2S$, $SO_2$, $NO$, etc.), and also some unreacted fossil fuel. Since there is tremendous amount of fossil fuel used for the purpose of producing energy, specific calculations will be given to illustrate its use also as a tracer in flow measurement.

Even though a number of approaches to do this can be found in various books discussing combustion and combustion engines in addition to examples in the chemical literature, one will be discussed in detail for the purpose of clarity.

Consider the burning of a mixture of pure hydrocarbon in air having an average empirical formula of $C_5H_{12}$. The average composition of carbon and hydrogen in this or other pure mixtures or compounds can be determined in a number of ways by chemical analysis. The combustion process can be expressed with the following unbalanced chemical equation:

$$C_5H_{12}+O_2+N_2 \rightarrow CO_2+CO+CH_4+C_5H_{12}+H_2O+N_2+O_2+CH_2O+NO+NH_3$$

Select one atom (e.g., carbon) in the starting material of interest (i.e., $C_5H_{12}$) and equate the mathematical product of the number of moles of this starting material times the number of carbon atoms (i.e., 5) found in the molecule (i.e., $C_5H_{12}$) to the sum of the individual mathematical products of the number of moles of each chemical product (containing one or more carbon atoms) times its number of carbon atoms per molecule. In cases where a significant amount of the chemically combined fossil fuel carbon is transformed into elemental solid carbon particles, special methods of analysis must be used or some correction factor for this ignored quantity of carbon must be applied. For example, we have:

[moles carbon]$_{reactants}$ = [moles carbon]$_{products}$ $$\left[\left(\frac{5 \text{ moles}_C}{1 \text{ mole}_{C_5H_{12}}}\right)\text{moles}_{(C_5H_{12})i}\right]_{reactants} =$$

$$\left[\left(\frac{1 \text{ mole}_C}{1 \text{ mole}_{CO_2}}\right)\text{moles}_{CO_2} + \left(\frac{1 \text{ mole}_C}{1 \text{ mole}_{CO}}\right)\text{moles}_{CO} + \right.$$

$$\left(\frac{1 \text{ mole}_C}{1 \text{ mole } CH_4}\right)\text{moles}_{CH_4} + \left(\frac{1 \text{ mole}_C}{1 \text{ mole } CH_2O}\right)\text{moles}_{CH_2O} +$$

$$\left.\left(\frac{5 \text{ moles}_C}{1 \text{ mole}_{C_5H_{12}}}\right)\text{moles}_{(C_5H_{12})f}\right]_{products}$$

where "i" and "f" refer to the initial and final states of the component before and after reaction, respectively. This terminology is used to designate that portion of an original component which has not undergone any change. Each term in the above molar equation can be divided by the component of volume in which each of the above components, i.e., $C_5H_{12}$, $O_2$, $N_2$, $CO_2$, $CO$, $CH_4$, $H_2O$, $N_2$, $O_2$, $CH_2O$ and $NO$, is present, resulting in units of moles per unit volume. Next, one can express the number of moles as mass per unit molecular weight for each component. This can be followed by expressing the ratio of mass per unit volume as a unit of concentration; the new set of units for each term will be concentration per unit molecular weight. In order to avoid confusion between the symbol "C" as used for carbon, the uncapitalized term "con" will be used wherever concentration needs to be used.

$$5\left(\frac{con}{M}\right)_{(C_5H_{12})i} =$$

$$\left(\frac{con}{M}\right)_{CO_2} + \left(\frac{con}{M}\right)_{CO} + \left(\frac{con}{M}\right)_{CH_4} +$$

-continued $$\left(\frac{con}{M}\right)_{CH_2O} + 5\left(\frac{con}{M}\right)_{(C_5H_{12})f}$$

Therefore, $$(m_1)_{t_2} - (m_1)_{t_1} =$$

$$\left(\frac{dm_{C_5H_{12}}}{dt}\right)\int_{t_1}^{t_2}\frac{con_1}{\frac{1}{5}\left(\frac{72}{44}\right)con_{CO_2} + \frac{1}{5}\left(\frac{72}{28}\right)con_{CO} + \frac{1}{5}\left(\frac{72}{16}\right)con_{CH_4} + \frac{1}{5}\left(\frac{72}{30}\right)con_{CH_2O} + con_{(C_5H_{12})f}}dt$$

$$con_{(C_5H_{12})i} = \frac{1}{5}\left(\frac{M_{(C_5H_{12})}}{M_{(CO_2)}}\right)con_{CO_2} +$$

$$\frac{1}{5}\left(\frac{M_{(C_5H_{12})}}{M_{(CO)}}\right)con_{CO} + \frac{1}{5}\left(\frac{M_{(C_5H_{12})}}{M_{(CH_4)}}\right)con_{CH_4} +$$

$$\frac{1}{5}\left(\frac{M_{(C_5H_{12})}}{M_{(CH_2O)}}\right)con_{CH_2O} + con_{(C_5H_{12})f}$$

where "con" is defined as concentration and M as Molecular weight of the specie designated in the subscript. After substituting the known molecular weights in the above mathematical equation we obtain:

$$con_{(C_5H_{12})i} = \frac{1}{5}\left(\frac{72}{44}\right)con_{CO_2} + \frac{1}{5}\left(\frac{72}{28}\right)con_{CO} +$$

$$\frac{1}{5}\left(\frac{72}{16}\right)con_{CH_4} + \frac{1}{5}\left(\frac{72}{30}\right)con_{CH_2O} + con_{(C_5H_{12})f}$$

When the concentration of the tracer, i.e., $con_{(C_5H_{12})i}$ in units of mass per unit volume, is inserted for $C_0$ in the basic total mass flow equation, i.e., $$(m_1)_{t_2} - (m_1)_{t_1} = \int_{t_1}^{t_2}\left(\frac{dm_o}{dt}\right)\frac{C_1}{C_o}dt$$

we obtain $$(m_1)_{t_2} - (m_1)_{t_1} = \int_{t_1}^{t_2}\left(\frac{dm_{C_5H_{12}}}{dt}\right)\frac{con_1}{con_{(C_5H_{12})i}}dt$$

where $con_{(C_5H_{12})i}$ is to be expressed in terms of its initial concentrations or its equivalent concentration (i.e., assuming it has not undergone any change since its time of introduction which can be calculated with both qualitative and quantative data on the resulting carbon containing decomposition products (including also the unreacted $C_5H_{12}$):

$$(m_1)_{t_2} - (m_1)_{t_1} =$$

$$\int_{t_1}^{t_2}\left(\frac{dm_{C_5H_{12}}}{dt}\right)\frac{con_1}{\frac{1}{5}\left(\frac{72}{44}\right)con_{CO_2} + \frac{1}{5}\left(\frac{72}{28}\right)con_{CO} + \frac{1}{5}\left(\frac{72}{16}\right)con_{CH_4} + \frac{1}{5}\left(\frac{72}{30}\right)con_{CH_2O} + con_{(C_2H_{12})f}}dt$$

Another approach would be to equate the hydrogen containing molecules, so the number of hydrogen atoms at the start is equal to those at the end of any reaction. Since water, which is one of these combustion products containing hydrogen, acts very "non-ideal" and tends to undergo a condensation reaction, it is usually not the preferred component to analyze, therefore hydrogen is usually not the chosen designated atom.

If the mass flow rate of the tracer is constant, the above equation becomes:

In the case where the only carbon material formed was carbon dioxide or the other carbon containing material was considered insignificant, the final equation becomes:

$$(m_1)_{t_2} - (m_1)_{t_1} = \int_{t_1}^{t_2}\left(\frac{dm_{C_5H_{12}}}{dt}\right)\frac{con_1}{\frac{1}{5}\left(\frac{72}{44}\right)con_{CO_2}}dt$$

Besides using carbon, hydrogen, or both as the products to be analyzed for calculating mass or volume flow, a mixture or pure component can be distributed throughout a composition such as a fossil fuel for the purpose of participating as a tracer. Rather than run an analysis for each of the organic species present in the combustion reaction, they could be analyzed for the total carbon concentration by means of a carbon flame ionization analyzer; this approach would be more direct in a number of cases and it would be satisfactory as far as tracer calculations are concerned. If our previous unbalanced chemical equation is written with this idea in mind, we obtain: $C_5H_{12} + O_2 + N_2 \rightarrow CO_2 + CO +$ single atom carbon special $+ H_2O + N_2 + O + NO + NH_3$.

In regards to determining the mass flow of the component of interest, this could also be (1) one of the components of the fuel or its reaction products (e.g., CO or $C_5H_{12}$), (3) a reaction product of combustion but not of the fuel (e.g., NO), or a product originally present before the combustion reaction occurred (e.g., in the air used for combustion).

In the case where instantaneous mass flow rates of the components of interest is desired, the same approach can be used as was done with the total mass flow determination when the tracer was a combustible fossil fuel; the difference is that no time integration is performed.

When the component which has been added (e.g., take the case of fuel, which itself can be the tracer, or a tracer can be added for the mass flow determination) undergoes a chemical or nuclear reaction, the amount or percent of reaction can be calculated from the mass introduction rates and the concentrations.

Total mass flow of at least one component of interest in a flow fluid mixture in a period of time is determined by the introduction of a tracer which is at least partly reactable into a flowing main fluid, at least partly reacting the mixture of tracer and the flowing main fluid in a reactor, analyzing the at least partly reacted fluid mixture to determine the concentration of at least one component of interest and at least one of any unreacted tracer and at least one tracer reaction product present in the fluid mixture, determining the concentration of the tracer that would be present in the fluid mixture if the tracer had not undergone a reaction from the concentration of at least one of any unreacted tracer and at least one tracer reaction product present in the fluid mixture, obtaining the mass flow rate of either the tracer that would be present in the flowing mixture if the tracer had not undergone a reaction or if at least one of the unreacted tracer remaining in the at least partly reacted fluid mixture and at least one tracer reaction product present in the fluid mixture from the known mass introduction rate of the tracer, and time integrating the product either: of at least one component of interest concentration, the reciprocal of the concentration of the tracer that would be present in the fluid mixture if the tracer had not undergone a reaction, and the mass flow rate of the tracer that would be present in the fluid mixture if the tracer had not undergone a reaction; or of at least one component of interest concentration, the reciprocal of the concentration of at least one of the unreacted tracer remaining in the at least partly reacted fluid mixture and at least one tracer reaction product present in the fluid mixture, and the mass flow rate of at least one of the unreacted tracer and at least one tracer reaction product present in the fluid mixture in accordance with the formula:

$$(m_1)_{t_2} - (m_1)_{t_1} = \int_{t_1}^{t_2} \frac{C_1}{C_o} \left( \frac{dm_o}{dt} \right) dt$$

where $(m_1)_{t_2} - (m_1)_{t_1}$ is the total mass flow of at least one component of interest over the time period $t_1$ to $t_2$, $$\left( \frac{dm_o}{dt} \right)$$

is either the mass flow rate of the tracer that would be present in the fluid mixture if the tracer had not undergone a reaction or the mass flow rate of at least one of the unreacted tracer remaining in the at least partly reacted fluid mixture and at least one tracer reaction product present in the fluid mixture, $C_1$ is the concentration of at least one component of interest, and $C_0$ is either the concentration of the tracer that would be present in the fluid mixture if the tracer had not undergone a reaction or the concentration of at least one of the unreacted tracer remaining in the at least partly reacted fluid mixture and at least one tracer reaction product present in the fluid mixture. In this method, the mass flow rate of either the tracer that would be present in the fluid mixture if the tracer had not undergone a reaction or of at least one of the unreacted tracer and at least one tracer reaction product is obtained from the mass introduction rate of the tracer.

The same basic mass equation given previously is used for particulate material; that is, a continuous analyzer is calibrated with a standard smoke, suspension, optical filter of a predetermined transmission (intensity and wavelength) which is equivalent to a definite concentration and type (size, shape, etc.) of the particulate material. An effective $C_1$ can be determined photometrically and expressed mathematically as $$C_1 = \frac{1}{a_{1l}} \log_{10} \frac{1}{T},$$

where T, the transmittance, is defined as the ratio of the intensity of the transmitted light per unit of incident light, "l" is the path length of the light absorption medium, and $a_1$ is the average absorption coefficient of the particulate material whose mass is being determined. If $C_1$ and "l" are expressed in units of mass per unit volume and length respectively, the $a_1$ will have units of area per unit mass. It is important here that the heterogeneous composition is uniform over the cross sectional area. For high smoke concentration, a shorter path length with greater width would be preferred. Shorter path lengths would decrease the likelihood of two or more particles blocking the same path of the directed, transmitted radiation (either electromagnetic or radioactive).

For determination of smoke mass arising from a combustion reaction of a fossil fuel, the fossil fuel itself is probably the best tracer. Collection of the smoke or particles from some other source, followed by continuous or periodic monitoring of the collected mass, e.g., by $\beta$-ray absorption, by change of frequency of a vibrating collector and the like is also practical.

The total volume flow of the main fluid or fluid mixture may also be determined for most compositions by the same general tracer technique used in determining the total mass of a component of interest. In such a determination, the flow system illustrated in FIG. 1 down through the pump 26 is utilized. Following the pump 26, a single analyzer 72, inverter 73, reciprocal proportionality factor 77, multiplier 75, time integrator 74, mass rate signal producing circuit 76 and multiplier 78, as shown in FIG. 2, are necessary to produce a total value output signal 79. It should be stated that if the volume flow of the incoming main fluid is to be determined, no inert fluid can be added unless the volume flow is known and then subtracted from the total volume flow which results. The mathematical computations to illustrate the theoretical accuracy of such a system are simplified relative to the total mass computations.

In the case where it is desired to determine the total volume flow of the main fluid flow with a variable mass injection rate of the tracer, the system illustrated in FIG. 4 is utilized. In such a determination, the flow system illustrated in FIG. 1 down through the pump 26 is used. Following pump 26, a single analyzer 100, reciprocal detector (an inverter) 101, reciprocal proportionality factor 103, mass rate signal 104, multiplier 102, and time integrator 105 are necessary to produce a total output signal 106.

In developing a simplified mathematical equation for total volume flow of a component of interest, the same symbol definitions are used as in the mass determination. The following equations are true based on reasoning similar to that for mass flow determination:

$$m_0 = C_0 V$$

$$\left(\frac{dm_o}{dt}\right) = C_o\left(\frac{dV}{dt}\right)$$

$$\left(\frac{dV}{dt}\right) = \left(\frac{dm_o}{dt}\right)\frac{1}{C_o}$$

In order to give meaning to any numerical value for volume flow, total or instantaneous, especially for easily compressible fluids, both temperature and pressure must be stated. If either or both the temperature and pressure are continuously varying at the point where the quantity of volume is assigned in the flow system, an exceedingly detailed continuous data bank would be needed. To avoid this, the description will deal with constant temperature and pressure at the point of assigning the numerical values, and if variations of temperature or pressure do occur, the volume should be thought of as being continuously referred back to some one set of conditions.

The total volumetric flow from time $t_1$ to $t_2$, that is, the time integral of the last above equation is given below:

$$\int_{(V)_{t_1}}^{(V)_{t_2}} dV = \int_{t_1}^{t_2} \left(\frac{dm_o}{dt}\right)\frac{dt}{C_o}$$

where $$\left(\frac{dm_o}{dt}\right)$$

is the instantaneous mass flow rate of the tracer and $C_0$ is the instantaneous concentration, in units of mass per unit volume, produced by said instantaneous mass flow rate of tracer.

Under the condition where $$\left(\frac{dm_o}{dt}\right)$$

is the mass rate of tracer as it passes through the cross sectional area 22, the following equation results:

$$(V)_{t_2} - (V)_{t_1} = \int_{t_1}^{t_2} \left(\frac{dm_o}{dt}\right)\frac{1}{C_o} dt$$

where the mass flow rate of the tracer can be a variable, but it must be known in addition to its concentration $C_0$, which it produces, both as a function of time.

When the mass flow rate of the tracer passing through the cross sectional area 22 equals a constant mass introduction rate of the tracer; that is $$\left(\frac{dm_o}{dt}\right) = \left(\frac{dm_o}{dt}\right)_o$$

equals a constant independent of time, the following final volumetric equation results:

$$(V)_{t_2} - (V)_{t_1} = \left(\frac{dm_o}{dt}\right)_o \int_{t_1}^{t_2} \frac{1}{C_o} dt$$

If the temperature, pressure and volumetric flow rate, (assuming ideal fluid behavior does result with the addition of $C_0$) of the flowing mixture are constant, then $$\frac{\left(\frac{dm_o}{dt}\right)_o}{C_o}$$

is also constant and it can be brought in front of the integral sign followed by its time integration as indicated in the following equation:

$$(V)_{t_2} - (V)_{t_1} = \left(\frac{dm_o}{dt}\right)_o \frac{1}{C_o} \int_{t_1}^{t_2} dt = \left(\frac{dm_o}{dt}\right)_o \frac{(t_2 - t_1)}{C_o}$$

The above integral is evaluated in the same manner as described for the total mass calculation with the exception that the concentration of only one component, that is, the tracer, is continuously analyzed. If the mass flow rate of the tracer passing through this cross sectional area only equals its mass introduction rate, but is not constant, the first equation would have to be used unless the tracer mass introduction rate is an average valuee; therefore, it is placed outside the integral sign. What is being said is that if the tracer introduction rate varies, the $$\left(\frac{dm_o}{dt}\right)$$

term must be integrated along with $C_0$. If the pressure, temperature and mass flow rate of the tracer is constant, the ratio of the mass introduction rate and the concentration resulting from that particular tracer mass flow rate, as analyzed for at the cross sectional area 22, is also constant.

If the total volumetric flow between times $t_1$ and $t_2$ are determined with the above equation, the total volumetric flow at a constant temperature and pressure can be computated for a known longer period of time with the following equation wherein $V_{t_3}$ and $V_{t_2}$ and $V_{t_1}$ are the total final, intermediate and initial volumes and where $t_3$, $t_2$ and $t_1$ are the final, intermediate and initial times, respectively:

$$V_{t_3} - V_{t_1} = (V_{t_2} - V_{t_1})\frac{(t_3 - t_1)}{(t_2 - t_1)}$$

The method of determining volumetric flow rate is useful in checking the constancy of the volumetric flow rate of the fluid for a definite temperature and pressure by continuously analyzing for $C_0$ and checking the constancy thereof.

In addition to being able to determine the instantaneous volumetric flow rate, it is also possible to determine the instantaneous linear velocity of the flowing fluid at the cross sectional area through which it passes. To determine either the linear velocity or the cross sectional area, one of the two should be known in addition to having the information needed to calculate the instantaneous flow rate. The following equations are used to make these two calculations:

$$\left(\frac{dl}{dt}\right) = \frac{1}{A}\left(\frac{dm_o}{dt}\right)\frac{1}{C_o}$$

$$A = \frac{1}{\left(\frac{dl}{dt}\right)}\left(\frac{dm_o}{dt}\right)\frac{1}{C_o}$$

where $$\left(\frac{dl}{dt}\right)$$

is the instantaneous linear velocity of the flowing fluid across the cross sectional area, A is the cross sectional area of interest, $$\left(\frac{dm_o}{dt}\right)$$

is the instantaneous mass flow rate of the tracer across this cross sectional area, and $C_0$ is the tracer concentration in units of mass per unit volume at cross sectional area A. For the determination of $$\left(\frac{dl}{dt}\right),$$

the cross sectional area A can be directly measuremented whereas in the determination of A, the instantaneous linear velocity $$\left(\frac{dl}{dt}\right)$$

can be measured by the introduction of a signal emitting or absorbing substance, such as a radioactive tracer material and the use of a signal absorbing or emitting analyzer, e.g., a Geiger or scintillation counter. One application would be to determine the total or instantaneous volume or mass flow of blood in the blood vessels of animals, including its instantaneous or average linear velocity, and the cross sectional area of the blood vessel at the point or points of interest. The main flow tube would be considered to be the blood vessel.

The instantaneous linear velocity of a flowing fluid mixture can be determined by injection of a tracer at a known mass rate into said flowing main fluid, mixing said flowing main fluid with said tracer, passing the mixture of tracer and main fluid through a cross sectional area, determining the cross sectional area, analyzing said mixture at said cross sectional area to determine the concentration of the tracer, determining the instantaneous mass flow rate of the tracer through the cross sectional area, and obtaining the product of the reciprocal of the concentration of the tracer, the mass flow rate of the tracer through the cross sectional area, and the reciprocal of said cross sectional area in accordance with the formula $$\left(\frac{dl}{dt}\right) = \left(\frac{dm_o}{dt}\right)\frac{1}{C}\frac{1}{A}$$

where $$\left(\frac{dl}{dt}\right)$$

is the instantaneous linear velocity of the flowing fluid, $$\left(\frac{dm_o}{dt}\right)$$

is the mass flow rate of the tracer through the cross sectional area, $C_0$ is the tracer concentration, and A is the cross sectional area.

The cross sectional area of a conduit of interest having a fluid flowing therethrough can be determined by the injection of a tracer at a known mass rate into said flowing main fluid, mixing said flowing fluid with said tracer, passing the mixture of tracer and main fluid through the cross sectional area of interest, determining the instantaneous linear velocity of the flowing fluid at the cross sectional area of interest, analyzing said mixture at said cross sectional area to determine the concentration of the tracer, determining the mass flow rate of tracer through the cross sectional area, and obtaining the product of the reciprocal of the concentration of the tracer, the mass flow rate of the tracer through said cross sectional area, and the reciprocal of the linear velocity of the flowing fluid at the cross sectional area of interest at the time of interest in accordance with the formula:

$$A = \left(\frac{dm_o}{dt}\right)\frac{1}{C}\frac{1}{\left(\frac{dl}{dt}\right)}$$

where A is the cross sectional area of interest, $$\left(\frac{dm_o}{dt}\right)$$

is the mass flow rate of the tracer through the cross sectional area, $C_0$ is the tracer concentration and $$\left(\frac{dl}{dt}\right)$$

is the linear velocity of the flowing fluid at said cross sectional area.

A tracer consisting of (1) a radioactive tagged atom, or (2) a body foreign to the blood, or (3) a substance already in the body like one of the minerals, halides, etc., vitamins, enzymes, and the like can be injected into the blood stream. This method would be carried out by injecting at a known mass rate, preferably constant, usually through a tube, e.g., hypodermic needle, and some of the flow is removed further downstream through another tube usually of the same type. Either continuous monitoring can be applied or a container sample can be sollected followed by a single analysis.

Although the ratio of the concentrations, that is, $$\frac{C_1}{C_o},$$

in the above equations refers to the concentrations of the fluid which is present in the main flow stream, the ratio should not be different at different temperatures and pressures in the analyzers as long as all analyzers have the fluid from the unknown mixture at the same temperature and pressure at which they were calibrated. This assumption is made assuming ideal fluid behavior, which is a good approximation in most cases if the variation in properties is not too great.

The concentration of tracer and component of interest, discussed in all the equations referred to so far, are for those conditions within the main flow tube. In order to express concentrations in terms of the conditions in the analyzer, assuming they are not the same conditions of temperature and pressure as in the main flow tube, the following equation which can be derived easily, can be used if gases are involved:

$$C_o = \frac{M_o \, 10^{-6}}{R \, Z} \frac{(P) \, (\text{ppm})_o}{(T)}$$

where $C_0$, $M_0$, P, T, $(\text{ppm})_0$ and Z are the tracer concentration (expressed in mass per unit volume), tracer molecular weight, ideal gas constant, total pressure, absolute temperature, tracer concentration in ppm by volume (same in main flow stream as in analyzer) and compressibility factor, respectively. As can be seen here, the pressure and temperature in the main flow tube (especially when gases are involved) enter into this equation. It is necessary to use this correction equation if either or both temperature and pressure are different in the main flow tube than in the analyzer compartment, when a single concentration variable is present in the equation, e.g., in the total volume flow equation, but if a ratio of concentrations are used, as in the mass flow equation, it would usually not matter.

Another means of expressing the tracer concentration (mass per unit volume) of a gaseous system in the main flow tube and analyzer is:

$$\frac{(C_o) \, 2}{(C_1) \, 1} = \frac{Z_1 \, P_2 \, T_1}{Z_2 \, P_1 \, T_2}$$

where the subscripts of 2 and 1 refer to the analyzer and mixture flow stream, respectively. Removal of the compressibility factors in this equation is usually possible by using conditions of temperature and pressure and fluids which are about the same in both the analyzer and the main flow tube. If the component used as the tracer is already present in the main fluid flow, then the following equation is used for the total mass flow, provided that the tracer mass introduction rate is constant:

$$(m_1)_{t2} - (m_1)_{t1} = \left(\frac{dm_o}{dt}\right)_o \int_{t_1}^{t_2} \frac{C_1}{(C_a - C_b)_o} \, dt$$

and the following equation is used for the total volume flow:

$$(V)_{t2} - (V)_{t1} = \left(\frac{dm_o}{dt}\right)_o \int_{t_1}^{t_2} \frac{1}{(C_a - C_b)_o} \, dt$$

If $(C_a - C_b)_0$ is a constant in either of the above volume or mass flow equations, it can be brought in front of the integral sign. In the case where the component $C_1$ and the added tracer are of the same kind; that is, $C_1 = C_b$, $C_a - C_b = C_a - C_1$.

Here $C_a$ is the sum of the concentrations of: the tracer component added and that which was already present in the main flow, and $C_b$ is the concentration of the tracer component which was already present. All the values of $C_a$, $C_b$ and $C_1$ must be expressed under the same conditions of temperature and pressure and in the same units of concentration. The remaining symbols have the same meaning as before.

In order to measure the increase in concentration of the tracer due to its introduction at a constant mass rate, it is continuously sampled at a point before the tracer introduction site and at a point where the tracer has become a part of the flowing uniform composition. For example, using a continuous flow analyzer with dual flow cells, it is possible to cancel out the effective upstream concentration of the tracer component which is present upstream of the site where the tracer is to be introduced at a constant mass rate. Here the reference flow cell has the original fluid passing through it from before the introduction and the sample flow cell has a mixture of the original plus that with the tracer addition, passing through it. If the tracer and component of interest are to be the same substance, a quantity of introduced tracer should be sufficiently great so the increase of tracer concentration can be calculated with sufficient accuracy.

When a variable mass introduction rate is used for the tracer when it is already present, the same mass and volume flow equations can be used with the exception that $$\left(\frac{dm_o}{dt}\right)$$

is behind the integral sign rather than before it and it must be known as a function of time. Unless the tracer mass introduction rate produces a concentration that is sufficiently greater than that which is already present, it will be difficult to relate the variable concentration increase of the tracer in the analyzer to its variable mass introduction rate which produced it at a definite time interval prior to its analysis. If all of this is based on a constant flowing fluid mixture in the main flow tube at a constant temperature and pressure, then $$\left(\frac{dm_o}{dt}\right)\left(C_a - C_b\right)_o$$

can be brought outside the integral sign, because it is independent of time.

In the case where the mass introduction rate of the tracer is not constant, difficulty arises when the amount introduced is based on a hard to calibrate metering valve. In order to calibrate a variable mass introduction device of this type for a tracer component, e.g., a liquid fossil fuel, or a component of interest, or for determining the mass introduction rate into a flowing fluid, a tracer, preferably at a constant mass introduction rate, is introduced into the above flowing fluid mixture.

The time required for a fluid which has a constant (assuming no temperature and pressure variation) volumetric flow rate in the main flow tube to reach and pass through the analyzer flow cells from the sample and reference taking point should be the same for this dual cell analyzer and others used in the same computation, i.e., theoretically the same original composition (except for the tracer because of its downstream addition) should reach both analyzer flow cells at the same time, including any other analyzer determining the concentration of other components of interest. When there is an introduction of the tracer, there should be an increase in concentration of this tracer in that sampling line which is located after the flowing main fluid has undergone a mixing process. For combustion processes where determination of $CO_2$ concentration is not necessary, the use of $CO_2$ as the tracer is practical, assuming the temperature of the flow system is at a high enough temperature to prevent condensation and absorption resulting in a significant percentage error.

In addition to continuous sampling, analysis and integration of instantaneous concentration values of the components of interest from the mixture flow stream, it is also possible to collect in chemically inert containers (usually flexible for a gas and rigid for a liquid) the total of the instantaneous sampling fluid.

The mixture continuously coming into the container is either (1) mixed continuously and the instantaneous composition of the mixture is continuously analyzed nondestructively, i.e., analysis has no effect on it, and the analyzed composition is returned to the original container, or (2) the total mixture is mixed uniformly, then it is analyzed. In the first method where the instantaneous fluid is collected during the period from $t_1$ to $t_2$ in the container, the same equation $$(m_1)_{t_2} - (m_1)_{t_1} = \left(\frac{dm_o}{dt}\right)_o \int_{t_1}^{t_2} \frac{C_1}{C_o} dt$$

is used but the instantaneous concentrations $C_1$ and $C_0$ are not the same, since they are instantaneous average concentration values resulting from the mixing of additional fluid from the sampling line with the total of that present previously in the container. For the second method we substitute the equation $$\int_{t_1}^{t_2} \frac{C_1}{C_o} dt = \frac{\overline{C_1}}{\overline{C_o}} (t_2 - t_1)$$

into the above. Therefore, $$(m_1)_{t_2} - (m_1)_{t_1} = \left(\frac{dm_o}{dt}\right)_o \frac{\overline{C_1}}{\overline{C_o}} (t_2 - t_1)$$

where $$\frac{\overline{C_1}}{\overline{C_o}}$$

refers to the ratio of the average value of $C_1$ divided by the average value of $C_0$.

In the second case, the same result is obtained as was obtained in the first because the flowing fluid mixture is the same, but only one set of analysis has to be run, i.e., the concentration of the component of interest $C_1$, and concentration of the tracer $C_0$; these are average values of the components in the main flow system. After the fluid is collected, it is mixed, e.g., if it is a liquid it can be stirred or shaken and if a gas it can be mixed by pressing on the flexible bag a number of times to mix the gas. Since only one concentration value is needed for each component to be analyzed, either a continuous or individual single sample analyzer need be used.

In these methods of collecting the fluid, the same principles hold as in the direct integration method including the equations (except the concentrations here are average, or instantaneous average values rather than instantaneous ones of a totally new portion of a fluid), the ratios $$\frac{C_1}{C_o}$$

are also not affected by changes of temperature and pressure between the main flow stream and the analyzers, but in the collection of the sample, the temperature, pressure and flow rate should be held at a constant value after the time the sample is removed from the main flow tube to the time it is analyzed for more accurate results. By storing the collected sample in a container and allowing it to stand for a period of time, it can be permitted to react if this is desirable (e.g., dissolving $NO_x$ auto exhaust gases in a Saltzmar reagent); but in most cases, reaction due to storage is a disadvantage; therefore, analysis is performed as soon as possible after collection of the sample.

It should be noted here that the equations $$\int_{t_1}^{t_2} \frac{C_1}{C_o} dt = \frac{\overline{C_1}}{\overline{C_o}} \int_{t_1}^{t_2} dt = \frac{\overline{C_1}}{\overline{C_o}} (t_2 - t_1)$$

are true if $C_0$ is a constant since the average of the sum of a number of ratios, usually does not equal the average of the sum of the values in the numerator divided by the average of the sum of the values in the denominator. The case where all denominator values are equal and constant is an exception. This is true when both the tracer mass introduction rate and the main fluid flow rate are constant.

If a constant fraction of the fluid from the main flow stream at a constant temperature and pressure is to be collected in a container, it is possible to introduce the tracer at a non-constant mass rate, and the general mass equation, i.e., $$(m_1)_{t_2} - (m_1)_{t_1} = \int_{t_1}^{t_2} \left(\frac{dm_o}{dt}\right) \frac{C_1}{C_o} dt$$

under conditions of a constant main fluid flow rate, resulting in $$\frac{\left(\frac{dm_o}{dt}\right)}{C_o}$$

equaling a constant, becomes $$(m_1)_{t_2} - (m_1)_{t_1} = \frac{\left(\frac{dm_o}{dt}\right)}{C_o} \int_{t_1}^{t_2} C_1 \, dt$$

As with the non-collected container sample, if the volumetric flow rate is constant in the main flow tube, the tracer should pass the cross sectional area at a rate equal or approximately equal to the mass introduction rate of the tracer, but at a different time. The time delay between introduction of the tracer and removal of the sample at the cross sectional area is based: (1) on the distance between tracer introduction site and location of the cross sectional area where the tracer is removed, and (2) on the main fluid flow rate.

The use of a light beam having both a reference and one or more sample wavelength bands where the reference wavelength band is not absorbed by a moving fluid but is blocked by particles within the gluid, while the tracer wavelength band and any number of component of interest wavelength bands are absorbed individually by the tracer and by the components of interest respectively in the moving fluid and are also blocked by the particles within the moving fluid, has also been considered.

By taking a log ratio of the intensities of the transmitted wavelength bands of the sample and reference component, the effect of the particles present in the flowing main fluid can be canceled out, and by using the sample beam wavelength for the tracer component with or without another sample beam wavelength for the component of interest, the total or instantaneous volume or mass flow, respectively, can be determined and a signal can be generated which is proportional to the concentration of the component of interest in a particle containing fluid, as for example, in the smokestack of a power plant. For a combustion process the fuel or one or more of its oxidation products, e.g., $CO_2$, $H_2O$, CO, and unburned fuel can be used as the tracer. The reference wavelength should not be absorbed by any component (except the particles) whose concentration does vary over the time interval when the measurements are taken. In this method we start with the basic mass equation:

$$(m_1)_{t_2} - (m_1)_{t_1} = \int_{t_1}^{t_2} \left(\frac{dm_o}{dt}\right) \frac{C_1}{C_o} \, dt$$

where $C_1 = \frac{1}{a_1 b_1} \log \frac{(I_x)_1}{(I_t)_1}$ and $C_o = \frac{1}{a_o b_o} \log \frac{(I_x)_o}{(I_t)_o}$ and $(I_x)_1 = \frac{(I_t)_R}{(I_o)_R} (I_o)_1 \quad (I_x)_o = \frac{(I_t)_R}{(I_o)_R} I_{o1}$ These terms, $C_1$ and $C_0$ and $(I_x)$, and $(I_x)_o$ are substituted into the basic mass equation, where the final equation is obtained:

$$(m_1)_{t_2} - (m_1)_{t_1} = \int_{t_1}^{t_2} \left(\frac{dm_o}{dt}\right) \frac{C_1}{C_o} \, dt = \int_{t_1}^{t_2} \left(\frac{dm_o}{dt}\right) \frac{\log \frac{(I_o)_1}{(I_t)_1} \frac{(I_t)_R}{(I_o)_R}}{\log \frac{(I_o)_o}{(I_t)_o} \frac{(I_t)_R}{(I_o)_R}} \, dt$$

where:
- $(I_x)_1$ = transmitted intensity partially blocked by particles at wavelength 1 for component 1, i.e., for component of interest.
- $(I_x)_0$ = as above, but at wavelength 0 and component 0, i.e., the tracer.
- $(I_x)_R$ = as above, but at wavelength R, i.e., the reference.
- $(I_t)_1$ = transmitted intensity partially blocked by particles at wavelength 1 for component 1.
- $(I_t)_0$ = as above but for wavelength 0 and component 0.
- $(I_t)_R$ = as above but for wavelength 0 and component 0.
- $(I_0)_R$ = transmitted intensity not blocked by particles or other varying components in the flowing mixture at wavelength R.
- $a_1$ and $a_0$ = electromagnetic radiation absorption coefficients.
- $b_1$ and $b_0$ = radiation path lengths, both are usually equal.

The apparatus to perform these analyses can be set up for passing a signal such as an electromagnetic one through a flowing fluid, and supplying an electronic signal to apparatus similar to that described in FIGS. 1, 2, 3 and 4 in order to obtain what is needed. The apparatus for these measurements can be supplied by the Environmental Data Corp. of California. It has a system which passes specific wavelength bands through the flowing fluid, e.g., that in a smokestack. The use of this method for volume or mass determination both instantaneous and total wherein a tracer is used is believed to be novel.

A method of determination in a flowing fluid mixture comprised of a main fluid, a tracer, and particles of the total mass flow of at least one component of interest selected from the group consisting of tracer, at least one reaction product of only the tracer, at least one component of the flowing main fluid, at least one reaction product of the tracer and the flowing main fluid and at least one reaction product of the flowing main fluid in a period of time is disclosed; comprising the introduction of an at least partly reactable tracer, at least some of whose reaction products are analyzable, into the flowing main fluid, reacting the fluid mixture of tracer and flowing main fluid to form at least one tracer reaction product, passing at least three analyzing signals through said reacted mixture wherein at least one of said signals is a reference signal which is blocked partially by the particles, at least one of said signals is a sample signal which is blocked partially by the particles and at least one component of interest, and at least one of said signals is the tracer signal which is blocked partially by the particles and at least one of the tracer and at least one analyzable reaction product of the tracer, obtaining the concentration of at least one component of interest and at least one of the tracer and at least one reaction product of the tracer from said analyzing signals, obtaining the mass flow rate of at least one of the tracer and at least one tracer reaction product, and time integrating the product of said mass flow rate of at least one of the tracer and at least one tracer reaction product, the concentration of at least one component of interest, and the reciprocal of at least one of the concentration of the tracer and the concentration of at least one tracer reaction product over a period of time from $t_1$ to $t_2$ in accordance with the formula:

$$(m_1)_{t_2} - (m_1)_{t_1} = \int_{t_1}^{t_2} \left(\frac{dm_o}{dt}\right) \frac{C_1}{C_o} dt$$

where $(m_1)_{t_2} - (m_1)_{t_1}$ is the total mass flow of at least one component of interest in the time period $t_1$ to $t_2$, $$\left(\frac{dm_o}{dt}\right)$$

is the mass flow rate of at least one of the tracer and at least one tracer reaction product, $C_1$ is the concentration of at least one component of interest, and $C_0$ is the concentration of at least one of the tracer at said tracer mass flow rate and at least one tracer reaction product at said mass flow rate of at least one tracer reaction product.

This method may also include the steps of introducing the tracer into the flowing main fluid at a known mass rate, and obtaining the mass flow rate of at least one of the tracer and at least one tracer reaction product from the known mass introduction rate of tracer. The analyzing signals may be electromagnetic radiation wavelength bands. The mass rate of tracer introduction may be constant or nearly constant and the flow of the flowing fluid mixture may be variable over the period of time. The mass rate of tracer introduction may be variable with time. Also, the concentration of at least one of the tracer and at least one tracer reaction product may be the concentration at said mass flow rate of at least one of the tracer and at least one tracer reaction product, at least one tracer reaction product may be carbon dioxide, and the tracer may be a fuel.

The total or instantaneous mass of one or more of the components present in a flowing fluid, and the total or instantaneous volume of a flowing main fluid or flowing fluid mixture can be measured with a specially calibrated analyzer-flow system calibration.

This is done by using a calibrated flow system consisting of a main flow tube with the following attachments: a tracer component (or component of interest) introduction site for introduction at a constant mass rate during time of calibration, a sampling tube and pump to transfer a continuous flow to the analyzers if analysis is not made directly on the fluid in the main flow tube, main flow by sending an analyzing signal through it or monitoring one from it, a continuous flow analyzer for each component to measure instantaneous concentrations on a continuous basis or one or more multi-component analyzers, a pumping system to maintain a continuous flow in the main fluid flow tube, an extra fluid flow inlet to maintain a constant fluid flow, and a mixer in the main flow tube to mix main and inlet fluid with introduced tracer fluid during analyzer calibration step. A constant temperature control system to maintain the flowing fluid at a constant temperature, a filter for particulate matter, and a vapor condenser at the entrance to the main flow tube or at some location before the flowing sample fluid enters the analyzer compartment of the analyzer may sometimes be necessary, depending on the composition of the main fluid. If this fluid is a gas, a critical orifice meter can be very useful to obtain a constant mass flow of an injected component, or a well-controlled gas regulator can be used. If the fluid is a liquid, a constant rate injection pump should be satisfactory.

Analyzers are calibrated by the introduction of a tracer and a component of interest, one at a time, at a constant mass flow rate into the main flow tube where each is mixed, but one at a time, with the main fluid flow, extra fluid is added if necessary to form a constant volumetric flow rate for the flowing mixture at a more changing temperature and pressure at every point inside the main flow tube and in the sampling line to the analyzers. The analysis is performed by transferring usually with a pump, of a continuous stream of the flowing fluid mixture into the continuous flow analyzers which are connected in parallel to each other, or it can be performed by sending or receiving an analyzing signal from or to the tracer and each component of interest flowing in the main flow tube. The values of the constant mass introduction, in units of mass per unit time, become the analyzer meter readings for that component, in that analyzer-flow tube system.

Analyzers can also be calibrated on a mass per unit time basis by first calibrating them in the usual manner (i.e., by passing the calibration fluid directly into the analyzer and not first through the main flow tube stream) in terms of ppm by volume, or some other concentration units based on the mole. This method is useful if there are a number of gases or fluids for which the meters are to be calibrated in units of volume per unit volume, here only one meter has to be calibrated by introducing a fluid at a known mass rate. To obtain this mass per unit time calibration on the other meters the following equation is used:

$$\left(\frac{dm_1}{dt}\right) = \left(\frac{dm_o}{dt}\right) \frac{M_1}{M_o} \frac{[C_1]}{[C_o]}$$

Symbol Definition $$\left(\frac{dm_1}{dt}\right) \text{ and } \left(\frac{dm_o}{dt}\right)$$

= instantaneous values of mass per unit time of component 1 and tracer (or reference component), respectively.

$M_1$ and $M_0$ = molecular weight of component 1 and tracer (or reference component), respectively.

$[C_1]$ and $[C_0]$ = concentration of component 1 and tracer (or reference component, respectively, expressed in terms of ppm by volume or some other mole dependent concentration.

If concentrations were expressed in units of mass per unit volume, the molecular weights would not be needed as part of the above mathematical equation and the equation becomes $$\left(\frac{dm_1}{dt}\right) = \left(\frac{dm_o}{dt}\right) \frac{C_1}{C_o}$$

which is the same equation as that which is used for the instantaneous mass flow determination.

For the determination of the total mass flow, either by the direct calibration of the analyzer-flow-tube system (i.e., the analyzer connected to the main flow stream) or indirectly by calibrating one analyzer with another, both connected in parallel to the main flow tube system, the following equation is used:

$$(m_1)_{t_2} - (m_1)_{t_1} = \int_{t_1}^{t_2} \left(\frac{dm_1}{dt}\right) dt$$

where $$\left(\frac{dm_1}{dt}\right)$$

in the instantaneous mass flow rate reading on the meter of the analyzer for the component of interest (component 1).

For example, if a carbon monoxide analyzer has already been calibrated in the usual manner, then a definite mass per unit time of carbon monoxide is introduced into the main flow tube continuously; the usual meter concentration (parts by volume) which corresponds to this constant mass injection value (i.e., mass per unit time), along with its molecular weight, can be used to determine the mass per unit time value of all the other analyzers because of the above equation.

A flow system can be calibrated for determining the total mass flow of a component of interest in a flowing fluid mixture in a period of time by injecting a first component of interest at a known constant mass rate into the main fluid flowing at a constant flow rate, mixing said component and said main fluid, passing the mixture of said first component of interest and said main fluid through a cross sectional area at a constant flow rate, calibrating a continuous flow analyzer in units of mass per unit time based on the known mass injection rate of said first component of interest, analyzing said mixture by means of said analyzer to determine the instantaneous mass flow rate of said first component of interest through the cross sectional area, and time integrating the analyzer signal representative of the instantaneous mass flow rate of said first component of interest through the cross sectional area over the period of interest, to obtain total mass flow of said first component interest in accordance with the equation:

$$(m_1)_{t_2} - (m_1)_{t_1} = \int_{t_1}^{t_2} \left(\frac{dm_1}{dt}\right) dt$$

where $(m_1)_{t_2} - (m_1)_{t_1}$ is the total mass flow of the first component of interest for the time period from $t_2$ to $t_1$ and $$\left(\frac{dm_1}{dt}\right)$$

is the mass flow rate of the first component of interest through the cross sectional area.

This last method can be expanded to include a method for determining the total mass flow of a second component of interest and for calibrating a second analyzer in units of mass per unit time comprising calibrating the first continuous flow analyzer and a second continuous flow analyzer in units of mass per unit volume, determining the concentration of said first and second components of interest by means of said first and second analyzers, obtaining the product of the ratio of the concentration of the first component of interest to the second component of interest and the mass injection rate of the first component of interest in accordance with the formula:

$$\left(\frac{dm_2}{dt}\right) = \left(\frac{dm_1}{dt}\right) \frac{C_2}{C_1}$$

where $$\left(\frac{dm_2}{dt}\right)$$

is the mass flow rate of the second component of interest, $$\left(\frac{dm_1}{dt}\right)$$

is the mass flow rate of the first component of interest, $C_2$ is the concentration of the second component of interest, $C_1$ is the concentration of the first component of interest, and time integrating the analyzer signal representative of the mass flow rate of the second component of interest over the time period of interest to obtain the total mass flow of said second component of interest in accordance with the formula:

$$(m_2)_{t_2} - (m_2)_{t_1} = \int_{t_1}^{t_2} \left(\frac{dm_2}{dt}\right) dt$$

where $(m_2)_{t_2} - (m_2)_{t_1}$ is the total mass flow of the second component in the time period $t_1$ to $t_2$ and $$\left(\frac{dm_2}{dt}\right)$$

is the mass flow rate of the second component of interest through the cross sectional area.

This method can be further expanded to include a method for determining the total mass flow of a second component of interest comprising determining the concentration of said first and second components of interest by means of said first and second analyzers, and time integrating the product of the ratio of the concentration of the mass flow rate of the first component of interest through the cross sectional area to the concentration of the first component of interest and the concentration of the second component of interest in accordance with the formula:

$$(m_2)_{t_2} - (m_2)_{t_1} = \int_{t_1}^{t_2} \frac{\left(\frac{dm_1}{dt}\right)}{C_1} C_2 \, dt$$

where $(m_2)_{t_2} - (m_2)_{t_1}$ is the total mass flow of the second component of interest in the time period $t_1$ to $t_2$, $$\left(\frac{dm_1}{dt}\right)$$

is the mass flow rate of the first component of interest through the cross sectional area, $C_1$ is the concentration in units of mass per unit volume of the first component of interest and $C_2$ is the concentration in mass per unit volume of the second component of interest.

As before, container samples can also be collected, analyzed, and the data can be used to determine total volume flow and total mass flow for a number of components present in a flowing fluid.

The procedure for this container method would be to inject the component of interest at a constant mass rate into a flow tube where the fluid is moving at a constant volumetric flow rate with temperature and pressure held constant (but may be different) at every point in the main flow tube and sampling line between the introduction site and the point of analysis, pass a sample of this fluid continuously into a container, mix uniformly, analyze for the component or components of interest, designate on this analyzer at the meter reading the value of the mass injection rate of that component which was used. (Note: Before the component of interest is passed into the analyzer, the analyzer must be zeroed in with a similar fluid but not containing the component of interest; also the analyzer must be adjusted so the calibrating component of interest gives a reasonable response on its meter reading.)

Now that the flow analyzer container system is calibrated, a sample of the flowing fluid containing the component of interest is passed through this calibrated tube-analyzer system and is collected in a container, mixed to a uniform composition and analyzed with the same analyzer whose meter had been calibrated previously. This meter reading resulting from the unknown sample is multiplied by the length of time the sample was collected and this will give the mass of the component of interest that has passed through the flow tube during the time when collection of the sample occurred.

Another approach where a container sample is involved would be where a known total mass of tracer is introduced at an unknown mass rate into a main fluid flowing at a constant flow rate (at a constant temperature and pressure) and mixed. A constant fraction of the total flow is passed continuously into a container, mixed, then analyzed for each component. With the following equation:

$$m_1 = m_o \frac{C_1}{C}$$

the total mass of component 1, $m_1$, passing through the cross sectional area is obtained by knowing how many grams of tracer, $m_o$, were introduced when the concentration of tracer in the collecting container is $C_0$ and the concentration of component 1 is $C_1$, both in units of mass per unit volume, over the period of time a constant fraction of the flowing fluid is being collected.

Structure for determining at least one of the total mass flow of at least one component of interest and the total volume flow of a flowing fluid mixture which comprises a main fluid and a tracer over a period of time comprises means for introducing a tracer at a constant or variable mass flow rate into the main fluid, means for mixing the tracer and main fluid, means for analyzing the fluid mixture for either the tracer concentration and at least one component of interest concentration or for the tracer concentration, all at the same time and at the same cross sectional area, and also in the same units of mass per unit volume, means for providing the reciprocal of the tracer concentration, means for obtaining the mass flow rate of the tracer from its known mass introduction rate, means for integrating either the reciprocal of the tracer concentration or the product of the reciprocal of the tracer concentration and the concentration of at least one component of interest over a period of time, and means for multiplying either the integrated reciprocal of the tracer concentration or the integrated product of the reciprocal of the tracer concentration and the concentration of at least one component of interest by the mass flow rate of tracer. The structure can include means for establishing a volumetric flow rate of the fluid which is not changing, means for keeping the temperature and pressure of the flowing fluid mixture from changing.

Structure for determining at least one of the total mass flow of at least one component of interest and the total volume flow of a flowing fluid mixture comprises a main fluid and a tracer in a main flow tube over a period of time. This structure comprises means for introducing a tracer into the main fluid, means for mixing the tracer with the main fluid, means for analyzing the fluid mixture for either the concentration of the tracer and the concentration of at least one component of interest or for the concentration of the tracer either directly in the main flow tube or by withdrawing a continuous sample, means for providing the reciprocal of the concentration of the tracer, means for obtaining the mass flow rate of the tracer at the same cross sectional area and at the same instantaneous times as the concentrations were determined from its known mass introduction rate, means for integrating the product of the mass flow rate of tracer and either the reciprocal of the tracer concentration and the concentration of at least one component of interest or the reciprocal of the tracer concentration over a period of time, means for keeping the volumetric flow rate from changing at every point. The total mass flow of at least one component of interest in a flowing fluid mixture can be determined for a specified period of time by the introduction of an analyzable tracer at the same cross sectional area and at the same instantaneous time as the concentrations were determined, from the known mass rate which can be constant or variable into the flowing main fluid, mixing the tracer with the main fluid, analyzing the mixed flowing mixture to determine the concentration of a tracer and at least one component of interest, all in the same units of mass per unit volume, integrating the determined concentration of at least one component in the flowing mixture over a period of time, and multiplying said time integrated concentration by the constant volumetric flow rate of the flowing mixture in accordance with the formula $$(m_1)_{t_2} - (m_1)_{t_1} = \left(\frac{dV}{dt}\right) \int_{t_1}^{t_2} C_1 \, dt$$

wherein $(m_1)_{t_2} - (m_1)_{t_1}$ is the total mass flow of the component of interest over the time period $t_1$ to $t_2$, $$\left(\frac{dV}{dt}\right)$$

is the constant volumetric flow rate of the flowing fluid mixture defined in accordance with the formula $$\left(\frac{dm_o}{dt}\right)\frac{1}{C_o}$$

wherein $$\left(\frac{dm_o}{dt}\right)$$

is the mass flow rate of the tracer also determined at the same cross sectional area and at the same instantaneous times as for the concentrations $C_0$ and $C_1$, and $C_0$ is the concentration of a tracer at said tracer mass flow rate in the flowing fluid mixture, the tracer mass flow rate is obtained from its mass introduction rate, and $C_1$ is the concentration of at least one component of interest. If the mass tracer introduction rate varies, the volumetric fluid flow rate of the mixture should not change, nor its temperature or pressure at every point between introduction of tracer and its analysis.

The total volume flow of a flowing fluid mixture at a constant volumetric flow rate comprising a main fluid and a tracer in a period of time can be determined. The method comprises the introduction of an analyzable tracer component at a known mass rate either constant or variable into the flowing main fluid, mixing the tracer with the main fluid, analyzing the flowing mixture to determine the concentration of the tracer, and multiplying the volumetric flow rate of the mixture by the time period of interest in accordance with the formula $$(V)_{t_2} - (V)_{t_1} = \left(\frac{dm_o}{dt}\right)\frac{1}{C_o}(t_2 - t_1)$$

where $(V)_{t_2} - (V)_{t_1}$ is the total volume flow over the time period, $(t_2 - t_1)$ is the time period, and $$\left(\frac{dm_o}{dt}\right)\frac{1}{C_o}$$

is the volumetric flow rate of the mixture with $$\left(\frac{dm_o}{dt}\right)$$

being the mass flow rate of the tracer obtained from its mass introduction rate and $C_0$ being the concentration in units of mass per unit volume of the tracer at said tracer mass flow rate.

The mass flow rate of at least one component of interest in a flowing fluid mixture comprising a main fluid and a tracer in a period of time can be determined. This method comprises the introduction of an analyzable tracer at a known mass rate, either variable or constant, into the flowing main fluid, mixing the tracer with the flowing main fluid, analyzing the flowing fluid mixture to determine the concentration of a tracer and at least one component of interest in the flowing mixture, obtaining the mass flow rate of the tracer from its mass introduction rate, determining the concentration of at least one component of interest, determining the concentration of the tracer at the mass flow rate of the tracer at the same cross sectional area and at the same instantaneous times as the concentrations were determined, from its known mass introduction rate, and obtaining the product of said mass flow rate of tracer, the reciprocal of the tracer concentration at the mass flow rate of tracer, and the concentration of at least one component of interest in accordance with the formula $$\left(\frac{dm_1}{dt}\right) = \left(\frac{dm_o}{dt}\right)\frac{C_1}{C_o}$$

wherein $$\left(\frac{dm_1}{dt}\right)$$

is the mass flow rate of at least one component of interest, $$\left(\frac{dm_o}{dt}\right)$$

is the mass flow rate of tracer obtained from its mass introduction rate, $C_1$ is the concentration of at least one component of interest, $C_0$ is the concentration of the tracer at said mass flow rate of tracer, where both concentrations are in the same units of mass per unit volume.

The mass flow rate of at least one component of interest in a flowing fluid mixture comprising at least a first and second fluid or the reaction products of at least one of the first and second fluid, said second fluid comprising a tracer. The method comprises the introduction of the tracer into at least said first fluid at a known mass rate, mixing the tracer with at least said first fluid to form said mixture, analyzing said mixture to determine the concentration in units of mass per unit volume of said tracer or at least one analyzable tracer reaction product and at least one component of interest in the mixture at the same cross sectional area and at the same time, obtaining the mass flow rate of the tracer or at least one analyzable tracer reaction product also at the same cross sectional area and at the same instantaneous times as the concentration determinations were made, from the known mass introduction rate of the tracer and obtaining the product of the concentration of at least one component of interest, the reciprocal of the tracer concentration or of the concentration of at least one analyzable tracer reaction product and the mass flow rate of tracer or at least one analyzable tracer reaction product in accordance with the formula $$\left(\frac{dm_1}{dt}\right) = \frac{C_1}{C_o}\left(\frac{dm_o}{dt}\right)$$

where $$\left(\frac{dm_1}{dt}\right)$$

is the mass flow rate of the component of interest, $$\left(\frac{dm_o}{dt}\right)$$

is the mass flow rate of tracer or at least one analyable tracer reaction product, $C_1$ is the concentration of at least one component of interest, and $C_0$ is the concentration of the tracer at the mass flow rate of the tracer or of at least one analyzable tracer reaction product at the mass flow rate of at least one of the analyzable tracer reaction products. If the volumetric flow rate of the flowing fluid mixture is not changing, the ratio of $$\frac{\left(\frac{dm_o}{dt}\right)}{C_o}$$

is a constant.

At least one of the total mass flow of a component of interest in a fluid mixture comprising a main fluid and a tracer and total volume flow of a fluid mixture in a period of time can be determined. The method comprises introducing an analyzable tracer into the main fluid and mixing, analyzing the fluid mixture to determine either the reciprocal of the tracer concentration and the concentration of at least one component of interest or the reciprocal of the tracer concentration, obtaining the mass flow rate of tracer at the same cross sectional area and at the same instantaneous times as the concentrations were determined from its known mass introduction rate, time integrating either of the reciprocal of the tracer concentration or the product of the reciprocal of the tracer concentration and the concentration of at least one component of interest, and obtaining the product of the mass flow rate of tracer and either the integrated reciprocal of the tracer concentration or the integrated product of the reciprocal of the tracer concentration and the concentration of at least one component of interest. If the volumetric flow rate of the flowing fluid mixture is not changing, while both its temperature and pressure are also not changing, the ratio of $$\frac{\left(\frac{dm_o}{dt}\right)}{C_o}$$

should be constant.

At least one of the total mass flow of a component of interest and the total volume flow of a fluid mixture comprising a main fluid and a tracer over a period of time may be determined by structure comprising means for introducing a tracer at a known mass introduction rate into the main fluid, means for mixing the introduced tracer with the main fluid, means for analyzing the fluid mixture to provide either a signal representative of the reciprocal of the concentration of the tracer or two signals one of which signals is representative of the reciprocal of the concentration of the tracer and the other of which signals is reresentative of at least one component of interest therein, all at the same cross sectional area and at the same times, means for obtaining a signal representative of mass flow rate of the tracer from its mass introduction rate, also at the same cross sectional area and time as for the analysis of the concentrations, means for combining either said signal representative of the mass flow rate of the tracer with said signal representative of the reciprocal of the concentration of the tracer or said signal representative of the mass flow rate of the tracer with the two signals one of which signals is representative of the reciprocal of the concentration of the tracer and the other of which signals is representative of the concentration of at least one component of interest, and means for time integrating at least one of said combined signals over a period of time. The structure can also includ means for keeping the volumetric flow rate of the flowing fluid mixture from changing, and means for keeping the temperature and pressure from changing.

The total volume flow of a flowing fluid mixture comprising a main fluid and a tracer in a period of time can be determined. The method comprises the introduction of an analyzable tracer at a known mass rate into the flowing main fluid, mixing the tracer with the main fluid flow, passing the mixed tracer and main fluid through a cross-sectional area, analyzing the mixture at the cross-sectional area to determine the concentration of the tracer in the fluid mixture, obtaining the mass flow rate of tracer at the same cross sectional area and at the same instantaneous time as the concentration were determined from its known mass introduction rate, and time integrating the product of the reciprocal of the concentration of the tracer at the mass flow rate of the tracer and the mass flow rate of the tracer over the time period in accordance with the formula:

$$(V)_{t2} - (V)_{t1} = \int_{t_1}^{t_2}\left(\frac{dm_o}{dt}\right)\frac{1}{C_o}\,dt$$

where $(V)_{t2}-(V)_{t1}$ is the total volume flow over the time period $t_1$ to $t_2$, $$\left(\frac{dm_o}{dt}\right)$$

is the mass flow rate of the tracer through the cross sectional area, and $C_0$ is the concentration of the tracer at the tracer mass flow rate. If the volumetric flow rate of the flowing fluid mixture is not changing, while both its temperature and pressure are also not changing, the ratio of $$\frac{\left(\frac{dm_o}{dt}\right)}{C_o}$$

should be constant.

The total mass flow of at least one component of interest in a flowing fluid mixture comprising a main fluid and a tracer in a period of time can be determined by the method comprising the introduction of an analyzable tracer into the flowing main fluid at a known mass rate, mixing the tracer with the flowing main fluid, analyzing the fluid mixture to determine the concentration of the tracer and at least one component of interest, obtaining the mass flow rate of tracer at the same cross sectional area and at the same instantaneous time as the concentrations from the mass introduction rate of the tracer, and time integrating the product of at least one component of interest concentration, the reciprocal of the tracer concentration, and the mass flow rate of the tracer over the time period in accordance with the formula:

$$(m)_{t_2} - (m)_{t_1} = \int_{t_1}^{t_2} \frac{C_1}{C_o} \left(\frac{dm_o}{dt}\right) dt$$

where $(m_1)_{t_2} - (m_1)_{t_1}$ is the total mass flow of at least one component of interest over the time period $t_1$ to $t_2$, $$\left(\frac{dm_o}{dt}\right)$$

is the mass flow rate of the tracer, $C_1$ is the concentration of at least one component of interest, and $C_0$ is the concentration of the tracer at said tracer mass flow rate, where both concentrations are in units of mass per unit volume. If the volumetric flow rate of the flowing fluid mixture is not changing while the pressure and temperature are also not changing, the ratio of $$\frac{\left(\frac{dm_o}{dt}\right)}{C_o}$$

should be constant.

Total mass flow of at least one component of interest in a flowing fluid mixture in a period of time is determined by the introduction of a tracer at a known mass rate which is at least partly reactable into a flowing main fluid, mixing the main fluid and tracer, at least partly reacting the mixture of tracer and the flowing main fluid in a reactor, analyzing the at least partly reacted fluid mixture to determine the concentration of at least one component of interest and at least one of any unreacted tracer and at least one tracer reaction product present in the fluid mixture, determining the concentration of the tracer that would be present in the fluid mixture if the tracer had not undergone a reaction from the concentration of at least one of any unreacted tracer and a least one tracer reaction product present in the fluid mixture, obtaining the mass flow rate of either the tracer that would be present in the flowing mixture if the tracer had not undergone a reaction or if at least one of the unreacted tracer remaining in the at least partly reacted fluid mixture and at least one tracer reaction product present in the fluid mixture at the same cross sectional area and at the same instantaneous time at which the concentrations are being obtained from the known mass introduction rate of the tracer, and time integrating the product either: of at least one component of interest concentration, the reciprocal of the concentration of the tracer that would be present in the fluid mixture if the tracer had not undergone a reaction, and the mass flow rate of the tracer that would be present in the fluid mixture if the tracer had not undergone a reaction; or of at least one component of interest concentration, the reciprocal of the concentration of at least one of the unreacted tracer remaining in the at least partly reacted fluid mixture and at least one tracer reaction product present in the fluid mixture, and the mass flow rate of at least one of the unreacted tracer and at least one tracer reaction product present in the fluid mixture in accordance with the formula:

$$(m_1)_{t_2} - (m_1)_{t_1} = \int_{t_1}^{t_2} \frac{C_1}{C_o} \left(\frac{dm_o}{dt}\right) dt$$

where $(m_1)_{t_2} - (m_1)_{t_1}$ is the total mass flow of at least one component of interest over the time period $t_1$ to $t_2$, $$\left(\frac{dm_o}{dt}\right)$$

is either the mass flow rate of the tracer that would be present in the fluid mixture if the tracer had not undergone a reaction or the mass flow rate of at least one of the unreacted tracer remaining in the at least partly reacted fluid mixture and at least one tracer reaction product present in the fluid mixture, $C_1$ is the concentration of at least one component of interest, and $C_o$ is either the concentration of the tracer that would be present in the fluid mixer if the tracer had not undergone a reaction or the concentration of at least one of the unreacted tracer remaining in the at least partly reacted fluid mixture and at least one tracer reaction product present in the fluid mixture; all concentration units in mass per unit volume. The mass flow rate of either the tracer that would be present in the fluid mixture if the tracer had not undergone a reaction or of at least one of the unreacted tracer and at least one tracer reaction product is obtained from the mass introduction rate of the tracer. The ratio is constant between the mass flow rate of either the tracer that would be present in the fluid mixture if the tracer had not undergone a reaction or if at least one of the unreacted tracer and at least one tracer reaction product and the concentration of either the tracer that would be present in the fluid mixture if the tracer had not undergone a reaction or if at least one of the unreacted tracer and at least one tracer reaction product in the flowing fluid mixture is constant.

The volume flow rate of a flowing fluid mixture can be determined by the introduction of a tracer into a flowing main fluid, mixing the tracer with the main fluid, analyzing the fluid mixture to determine the concentration of the tracer and expressing it in units of mass per unit volume, obtaining the mass flow rate of tracer at the same cross sectional area and at the same instantaneous times as the other concentrations were determined from the mass introduction rate of the tracer, obtaining the product of the reciprocal of the tracer concentration and the mass flow rate of the tracer in accordance with the formula:

$$\left(\frac{dV}{dt}\right) = \left(\frac{dm_o}{dt}\right)\frac{1}{C_o}.$$

where $$\left(\frac{dV}{dt}\right)$$

is the volume flow rate of the flowing fluid mixture, $$\left(\frac{dm_o}{dt}\right)$$

is the mass flow rate of the tracer, and $C_0$ is the concentration of the tracer in units of mass per unit volume.

The mass flow rate of at least one component of interest in a flowing fluid mixture is determined by the introduction of an analyzable tracer into the flowing main fluid, mixing the tracer with the main fluid, analyzing the fluid mixture to determine the concentration of the tracer and at least one component of interest in the fluid mixture, obtaining the mass flow rate of the tracer at the same cross sectional area and at the same instantaneous times as the other concentrations were obtained from the tracer mass introduction rate, and obtaining the product of the reciprocal of the concentration of the tracer, the concentration of at least one component of interest, and the mass flow rate of the tracer in accordance with the formula:

$$\left(\frac{dm_1}{dt}\right) = \frac{C_1}{C_o}\left(\frac{dm_o}{dt}\right)$$

where $$\left(\frac{dm_1}{dt}\right)$$

is the mass flow rate of the component of interest, $C_1$ is the concentration of the component of interest, $C_o$ is the concentration of the tracer at the mass flow rate of the tracer, and $$\left(\frac{dm_o}{dt}\right)$$

is the mass flow rate of the tracer. At a non-changing volumetric flow rate along with a non-changing temperature and pressure, the ratio of $$\frac{\left(\frac{dm_o}{dt}\right)}{C_o}$$

is a constant.

The linear velocity of a flowing fluid mixture comprised of a main fluid and a tracer can be determined by the introduction of a tracer into a flowing main fluid, mixing the flowing main fluid with the tracer, passing the fluid mixture of tracer and main fluid through a cross sectional area, determining the cross sectional area, determining the mass flow rate of the tracer through the cross sectional area at the same instantaneous times as the other concentration is determined from the tracer introduction rate, analyzing said mixture to determine the concentration of the tracer at said mass flow rate of tracer at the cross sectional area, and obtaining the product of the reciprocal of the concentration of the tracer, the mass flow rate of the tracer through the cross sectional area, and the reciprocal of the cross sectional area in accordance with the formula:

$$\left(\frac{dl}{dt}\right) = \left(\frac{dm_o}{dt}\right)\frac{1}{C_o}\frac{1}{A}$$

where $$\left(\frac{dl}{dt}\right)$$

is the linear velocity of the flowing fluid mixture, $$\left(\frac{dm_o}{dt}\right)$$

is the mass flow rate of the tracer, and $C_0$ is the tracer concentration in units of mass per unit volume, all at said cross sectional area A. In this method it is desirable to hold the tracer mass introduction rate constant and to hold the volumetric flow rate of the flowing fluid, the pressure and temperature constant if possible.

The cross sectional area of interest through which a fluid mixture comprised of a main fluid and a tracer passes can be determined. The method comprises introducing a tracer into a flowing main fluid at a known mass rate, passing the fluid mixture of tracer and main fluid through the cross sectional area of interest, determining the linear velocity of the flowing fluid at the cross sectional area of interest, analyzing said mixture to determine the concentration of the tracer, determining the mass flow rate of tracer through the cross sectional area and at the same instantaneous times as with the concentration from the mass introduction rate of the tracer, obtaining the mass flow rate of tracer through the cross sectional area from the known mass introduction rate of tracer, and obtaining the product of the reciprocal of the concentration of the tracer, the mass flow rate of the tracer through said cross-sectional area, and the reciprocal of the linear velocity of the flowing fluid at the cross sectional area of interest at the time of interest in accordance with the formula:

$$A = \left(\frac{dm_o}{dt}\right) \cdot \frac{1}{C_o} \cdot \frac{1}{\left(\frac{dl}{dt}\right)}$$

where A is the cross sectional area of interest, $$\left(\frac{dm_o}{dt}\right)$$

is the mass flow rate of the tracer through the cross sectional area, $C_0$ is the tracer concentration in units of mass per unit volume and $$\left(\frac{dl}{dt}\right)$$

is the linear velocity of the flowing fluid at said cross sectional area.

A method of determination in a flowing fluid mixture comprised of a main fluid, a tracer, and particles of the total mass flow of at least one component of interest selected from the group consisting of tracer, at least one reaction product of only the tracer, at least one component of the flowing main fluid, at least one reaction product of the tracer and the flowing main fluid and at least one reaction product of the flowing main fluid in a period of time is disclosed comprising the introduction of an at least partly reactable tracer at a known mass introduction rate, at least some of whose reaction products are analyzable, into the flowing main fluid, mixing and reacting the fluid mixture of tracer and flowing main fluid to form at least one tracer reaction product, passing at least three analyzing signals through said reacted mixture wherein at least one of said signals is a reference signal which is blocked partially by the particles, at least one of said signals is a sample signal which is blocked partially by the particles and at least one component of interest, and at least one of said signals is the tracer signal which is blocked partially by the particles and at least one of the tracer and at least one analyzable reaction product of the tracer, obtaining the concentration of at least one component of interest and at least one of the tracer and at least one reaction product of the tracer from said analyzing signals, obtaining the mass flow rate of at least one of the tracer and at least one tracer reaction product at the same cross sectional area and at the same instantaneous times as is being done with the other concentrations from the known tracer mass introduction rate, and time integrating the product of said mass flow rate of at least one of the tracer and at least one tracer reaction product, the concentration of at least one component of interest, and the reciprocal of at least one of the concentration of the tracer and the concentration of at least one tracer reaction product over a period of time from $t_1$ to $t_2$ in accordance with the formula:

$$(m_1)_{t_2} - (m_1)_{t_1} = \int_{t_1}^{t_2} \left(\frac{dm_o}{dt}\right) \frac{C_1}{C_o} dt$$

where $(m_1)_{t_2} - (M_1)_{t_1}$ is the total mass flow of at least one component of interest in the time period $t_1$ to $t_2$, $$\left(\frac{dm_o}{dt}\right)$$

is the mass flow rate of at least one of the tracer and at least one tracer reaction product, $C_1$ is the concentration in units of mass per unit volume of at least one component of interest, and $C_0$ is the concentration also in units of mass per unit volume of at least one of the tracer at said tracer mass flow rate and at least one tracer reaction product at said mass flow rate of at least one tracer reaction product. If the volumetric flow rate of the flowing fluid mixture is not changing at a non-changing temperature and pressure, the ratio of $$\frac{\left(\frac{dm_o}{dt}\right)}{C_o}$$

is constant.

The total volume flow of a flowing fluid mixture in a period time can be determined by a method comprising the introduction of a tracer into a flowing main fluid at a known mass flow rate, mixing the tracer with the main fluid flow, passing the fluid mixture of the tracer and main fluid through a cross sectional area, continuously collecting a portion of said mixture in a container at said cross sectional area, mixing said portion in said container, analyzing said mixed portion to determine the average concentration of the tracer, obtaining the average mass flow rate of the tracer through the cross sectional area from its mass introduction rate, obtaining a reciprocal of the average tracer concentration, and obtaining the product of said reciprocal and the average mass flow rate of the tracer through the cross sectional area and the time during which the portion is being collected in accordance with the formula:

$$(V)_{t_2} - (V)_{t_1} = \left(\frac{dm_o}{dt}\right)\frac{1}{C_o}(t_2 - t_1)$$

where $(V)_{t_2} - (V)_{t_1}$ is the total volume of the flowing fluid mixture in a period of time from $t_1$ to $t_2$, $$\left(\frac{dm_o}{dt}\right)$$

is is the average mass flow rate of tracer through the cross sectional area, $$\frac{1}{C_o}$$

is the average concentration of the tracer in said container in units of mass per unit volume, and $(t_2 - t_1)$ is the period of time during which said portion of said mixture is being collected.

The total mass of a component of interest in a flowing fluid mixture in a period of time can be determined by a method comprising the introduction of an analyzable tracer into a flowing main fluid at a known mass rate, passing the flowing fluid mixture comprised of the tracer and main fluid through a cross sectional area, collecting for a period of time at said cross sectional area a constant fraction of said flowing fluid mixture in a container, mixing said collected constant fraction in said container, analyzing said mixed constant fraction to determine the average concentration of the tracer and the average concentration of at least one component of interest, obtaining the reciprocal of said average concentration of the tracer, obtaining the average mass flow rate of the tracer through the cross sectional area from the tracer mass injection rate, and obtaining the product of the reciprocal of the average concentration of the tracer, the average concentration of at least one component of interest, the average mass flow rate of the tracer through the cross sectional area, and the time during which the constant fraction of the flowing fluid mixture was being collected in said container in accordance with the formula:

$$(m_1)_{t_2} - (m_1)_{t_1} = \left(\frac{dm_o}{dt}\right)\frac{\overline{C_1}}{\overline{C_o}}(t_2 - t_1)$$

where $(m_1)_{t_2} - (m_1)_{t_1}$ is the total mass flow of at least one component of interest in the period of time $t_1$ to $t_2$, $$\left(\frac{dm_o}{dt}\right)$$

is the average mass flow rate of the tracer through the cross sectional area, $\overline{C_o}$ is the average concentration of the tracer, and $\overline{C_1}$ is the average concentration of at least one component of interest, both concentrations being in units of mass per unit volume.

What I claim as my invention is:

1. The method of determination of the total mass flow of at least one component of interest in a flowing fluid mixture in a period of time comprising the introduction of a tracer which is at least partly reactable into a flowing main fluid, at least partly reacting at least one of the tracer and the mixture of tracer and the flowing main fluid in a reactor, analyzing the reacted fluid mixture to determine the concentration of at least one component of interest which may also be one from the group of unreacted tracer and tracer reaction products and also analyzing at least one of any unreacted tracer and at least one of the tracer reaction products present in the fluid mixture, determining the concentration of the tracer that would be present in the fluid mixture if the tracer had not undergone a reaction from the concentration of at least one from the group of any unreacted tracer and tracer reaction products present in the fluid mixture, obtaining the mass flow rate of the tracer that would be present in the flowing mixture if the tracer had not undergone a reaction from the mass introduction rate of the tracer, and time integrating the product of the concentration of at least one component of interest concentration, the reciprocal of the concentration of the tracer that would be present in the fluid mixture if the tracer had not undergone a reaction, and the mass flow rate of the tracer that would be present in the fluid mixture if the tracer had not undergone a reaction in accordance with the formula:

$$(m_1)_{t_2} - (m_1)_{t_1} = \int_{t_1}^{t_2} \frac{C_1}{C_o}\left(\frac{dm_o}{dt}\right)dt$$

where $(m_1)_{t_2} - (m_1)_{t_1}$ is the total mass flow of at least one component of interest over the time period $t_1$ to $t_2$, $$\left(\frac{dm_o}{dt}\right)$$

is the mass flow rate of the tracer that would be present in the fluid mixture if the tracer had not undergone a reaction, $C_1$ is the concentration of at least one component of interest which may also be one from the group of unreacted tracer and tracer reaction products, and $C_o$ is the concentration of the tracer that would be present in the fluid mixture if the tracer had not undergone a reaction.

2. The method as set forth in claim 1, wherein the reactor is a furnace.

3. The method as set forth in claim 1, wherein the reactor is a combustion engine.

4. A method of determination in a flowing fluid mixture comprised of a main fluid, a tracer, and particles of the total mass flow of at least one component of interest selected from the group consisting of tracer, at least one reaction product of only the tracer, at least one component of the flowing main fluid, at least one reaction product of the tracer and the flowing main fluid and at least one reaction product of the flowing main fluid in a period of time comprising the introduction of an at least partly reactable tracer, at least some of whose reaction products are analyzable, into the flowing main fluid, reacting the fluid mixture of tracer and flowing main fluid to form at least one tracer reaction product, passing at least three analyzing signals through said reacted mixture wherein at least one of said signals is a reference signal which is blocked partially by the particles, at least one of said signals is a sample signal which is blocked partially by the particles and at least one component of interest, and at least one of said signals is the tracer signal which is blocked partially by the particles and at least one of the tracer and at least one analyzable reaction product of the tracer, obtaining the concentration of at least one component of interest and at least one of the tracer and at least one reaction product of the tracer from said analyzing signals, obtaining the mass flow rate of at least one of the tracer and at least one tracer reaction product, and time integrating the product of said mass flow rate of at least one of the tracer and at least one tracer reaction product, the concentration of at least one component of interest, and the reciprocal of at least one of the concentration of the tracer and the concentration of at least one tracer reaction product over a period of time from $t_1$ to $t_2$ in accordance with the formula:

$$(m_1)_{t_2} - (m_1)_{t_1} = \int_{t_1}^{t_2}\left(\frac{dm_o}{dt}\right)\frac{C_1}{C_o}dt$$

where $(m_1)_{t_2} - (m_1)_{t_1}$ is the total mass flow of at least one component of interest in the time period $t_1$ to $t_2$, $$\left(\frac{dm_o}{dt}\right)$$

is the mass flow rate of at least one of the tracer and at least one tracer reaction product, $C_1$ is the concentration of at least one component of interest, and $C_0$ is the concentration of at least one of the tracer at said tracer mass flow rate and at least one tracer reaction product at said mass flow rate of at least one tracer reaction product.

5. The method as set forth in claim 4, wherein the analyzing signals are electromagnetic radiation.

6. The method as set forth in claim 4, wherein the tracer is a fuel.

7. The method of determination of the total mass flow of at least one component of interest in a flowing fluid mixture in a period of time comprising the introduction of a tracer which is at least partly reactaale into a flowing main fluid, at least partly reacting at least one of the tracer and the mixture of tracer and the flowing main fluid in a reactor, choosing one of the atoms contained in the above mentioned tracer which was introduced into the flowing main fluid, analyzing for the concentration of at least one component of interest and at least one of any unreacted tracer and its tracer reaction products, determining the concentration of at least one type of designated atom present originally in the tracer that was introduced into the main fluid, obtaining the mass flow rate of the designated type of atom present originally in the tracer from the mass introduction rate of the tracer, and time integrating the methamaterial product of the mass flow rate of the designated type of atom present originally in the tracer, the reciprocal of the concentration of the designated type of atom present originally in the tracer and the concentration of the component of interest in accordance with the formula:

$$(m_1)_{t_2} - (m_1)_{t_1} = \int_{t_1}^{t_2} \frac{C_1}{C_o} \left(\frac{dm_o}{dt}\right) dt$$

where $(m_1)_{t_2} - (m_1)_{t_1}$ is the total mass flow of at least one component of interest over the time period $t_1$ to $t_2$ $$\left(\frac{dm_o}{dt}\right)$$

is the mass flow rate of the designated type of atom present originally in the tracer, $C_0$ is the concentration of the designated atom present originally in the tracer, and $C_1$ is the concentration of the component of interest.

* * * * *